(12) United States Patent
Chan et al.

(10) Patent No.: US 9,642,360 B2
(45) Date of Patent: May 9, 2017

(54) ANTIMICROBIAL POLYMERS FORMED BY BULK POLYADDITION

(71) Applicants: International Business Machines Corporation, Armonk, NY (US); AGENCY FOR SCIENCE, TECHNOLOGY AND RESEARCH, Singapore (SG)

(72) Inventors: Julian M. W. Chan, Ottawa (CA); James L. Hedrick, Pleasanton, CA (US); Robert J. Ono, San Jose, CA (US); Jye Yng Teo, Singapore (SG); Yi Yan Yang, Singapore (SG); Mu San Zhang, San Jose, CA (US)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 0 days.

(21) Appl. No.: 14/749,764

(22) Filed: Jun. 25, 2015

(65) Prior Publication Data

US 2016/0374335 A1  Dec. 29, 2016

(51) Int. Cl.
*A61K 31/74*  (2006.01)
*A01N 33/12*  (2006.01)
*C08G 73/02*  (2006.01)

(52) U.S. Cl.
CPC ........... *A01N 33/12* (2013.01); *C08G 73/024* (2013.01); *C08G 73/0206* (2013.01); *C08G 73/0213* (2013.01)

(58) Field of Classification Search
None
See application file for complete search history.

(56) References Cited

U.S. PATENT DOCUMENTS

| 3,265,663 | A | 8/1966 | Lloyd |
| 6,955,806 | B2 | 10/2005 | Fitzpatrick et al. |
| 8,349,303 | B1 * | 1/2013 | Phillips ............... C11D 3/0078 424/78.04 |
| 2006/0002887 | A1 | 1/2006 | Fitzpatrick et al. |

FOREIGN PATENT DOCUMENTS

| EP | 0825175 | * | 2/1998 | ........... C07C 211/63 |
| EP | 0825175 | A1 | 2/1998 | |

OTHER PUBLICATIONS

U.S. Appl. No. 14/223,630, filed Mar. 24, 2014.
Kolpin, et al., "Pharmaceuticals, Hormones, and Other Organic Wastewater Contaminants in U.S. Streams, 1999-2000: A National Reconnaissance", Environ. Sci. Technol. 2002, 36, 1202-1211.
Singer, et al., "Triclosan: Occurrence and Fate of a Widely Used Biocide in the Aquatic Environment: Field Measurements in Wastewater Treatment Plants, Surface Waters, and Lake Sediments", Environ. Sci. Technol., 2002, 36 (23), pp. 4998-5004.

* cited by examiner

*Primary Examiner* — Anna Falkowitz
(74) *Attorney, Agent, or Firm* — Michael R. Roberts

(57) ABSTRACT

Cationic antimicrobial polymers have been synthesized by a bulk addition polymerization of a nucleophilic agent comprising two tertiary amines and an electrophilic agent that comprises two leaving groups and an aromatic ring between the leaving groups. The reaction solvent for the polymerization is chosen to allow precipitation of the cationic polymer at the polymerization temperature, thereby limiting molecular weight. Quaternization and polymerization occur concurrently. The cationic polymers can be highly active against Gram-negative and Gram-positive microbes, and/or fungi. The cationic polymers can also be non-hemolytic and non-cytotoxic at the effective concentration against the microbes.

23 Claims, 20 Drawing Sheets

ANTIMICROBIAL POLYMERS FORMED BY BULK POLYADDITION

PARTIES TO A JOINT RESEARCH AGREEMENT

This invention was made under a joint research agreement between International Business Machines Corporation and the Agency For Science, Technology and Research.

BACKGROUND

The present invention relates to antimicrobial polymers formed by bulk polyaddition, and more specifically, to cationic polymers having quaternary backbone nitrogens formed by bulk polyaddition.

Antimicrobial agents are commonly used in personal care products to inhibit microbial growth for preventing infections and product decomposition. Most antimicrobial agents used in these products are small molecules, including anilides (e.g., triclocarban), bis-phenols (e.g., triclosan), biguanides (e.g., chlorhexidine) and quaternary ammonium compounds (e.g., cetylpyridium chloride and cetrimide). Among them, triclosan is one of the most extensively used compounds. Triclosan is present in more than 50% of consumer products including soap, deodorant, toothpaste, mouth wash, cosmetics (e.g., GARDEN BOTANIKA® Powder Foundation, Mavala Lip Base, Jason Natural Cosmetics and MOVATE® Skin Litening Cream HQ), cleaning supplies, kitchen utensils, children's toys, bedding, socks, shoes and garbage bags. It is effective against Gram-positive bacteria, while it has little activity against *Pseudomonas aeruginosa* (*P. aeruginosa*, Gram-negative bacteria) and molds. At high concentrations, triclosan is biocidal with multiple cytoplasmic and membrane targets. However, at low concentrations, it is bacteriostatic by inhibiting fatty acid synthesis. On the other hand, triclosan has cumulative and persistent effects on the skin. It was found in human milk and urine samples. At minimal concentrations of triclosan (<1 microgram/L) and chlorine (<1 mg/L), common household tap water levels, triclosan can degrade to form toxic derivatives, 2,4-dichlorophenol and 2,4,6-trichlorophenol. Moreover, in sunlight and wastewater chlorine treatment, triclosan also forms highly toxic carcinogenic dioxin-like compounds. After use, triclosan is discharged into water. Triclosan was found in 85 out of 139 streams and rivers in 30 states in the US, and is toxic to aquatic species (Kolpin, D. W., et al., "Pharmaceuticals, Hormones, and Other Organic Wastewater Contaminants in U.S. Streams, 1999-2000: A National Reconnaissance", Environ. Sci. Technol. 2002, 36, 1202-1211). Triclosan was detected in sediments in a Swiss lake as far back as 1960s (Singer, H., et al., "Triclosan: Occurrence and Fate of a Widely Used Biocide in the Aquatic Environment: Field Measurements in Wastewater Treatment Plants, Surface Waters, and Lake Sediments", Environ. Sci. Technol., 2002, 36 (23), pp 4998-5004). Triclosan resistance has been found in various strains of microbes. Therefore, the use of triclosan in consumer products is likely to be banned in Europe and in the USA.

Many strains of bacteria spores (e.g., *Clostridium* species), Gram-positive (e.g., mycobacteria) and Gram-negative bacteria (*P. aeruginosa*) have intrinsic resistance to the antimicrobial agents listed above. Moreover, these antimicrobial agents are not effective against biofilms. For example, *Serratia marcescens* and *Burkolderia cepacia* biofilms were found in disinfectant chlorhexidine solution, *Pseudomonas* biofilm in iodophor antiseptics and on the interior surface of polyvinyl chloride pipes used in the production of providone-iodine antiseptics. One of the major concerns is that resistant biofilms may lead to cross-resistance and co-resistance of clinically used antimicrobial agents, a potential public health risk.

Most small molecular antimicrobial agents do not physically damage the cell wall but penetrate into the target microorganism and act on specific targets. As a consequence, bacterial morphology is preserved and the bacteria can easily develop resistance. Antimicrobial peptides (AMPs) have been explored as an alternative. AMPs (e.g., magainins, alamethicin, protegrins and defensins) do not have a specific target in microbes. They interact with microbial membranes based on electrostatic interaction, thereby inducing damage to the microbial membranes by forming pores in the membranes. The physical nature of this action prevents microbes from developing resistance to AMPs. Although efforts have been made to design synthetic peptides with various structures over the last two decades, high manufacturing cost has limited their application in personal care products.

A number of cationic polymers that mimic the facially amphiphilic structure and antimicrobial functionalities of peptides have been proposed as a better approach, as they can be more easily prepared at low cost and large scale compared to peptides. For example, antimicrobial polynorbornene and polyacrylate derivatives, and pyridinium copolymers were synthesized either from amphiphilic monomers (homopolymers) or from a mixture of a cationic (hydrophilic) monomer and a hydrophobic comonomer (random copolymers). However, most antimicrobial polymers reported in the literature require several steps of synthesis that would lead to high production cost.

A need continues for more environmentally compatible antimicrobial agents used in personal care products that can rapidly kill multidrug-resistant bacteria and fungi, remove biofilms, and prevent drug resistance.

SUMMARY

Accordingly, a cationic polymer is disclosed comprising a cationic repeat unit of formula (C-1):

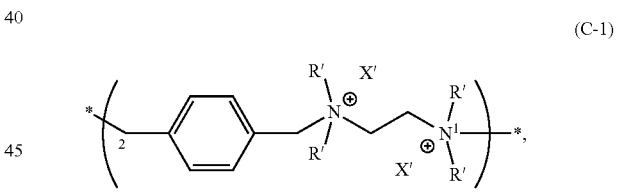

(C-1)

wherein
each X' is an independent negative-charged counterion, and
each R' is an independent monovalent radical selected from the group consisting of methyl, ethyl and propyl.

Also disclosed is a cationic polymer comprising a cationic repeat unit of formula (C-5):

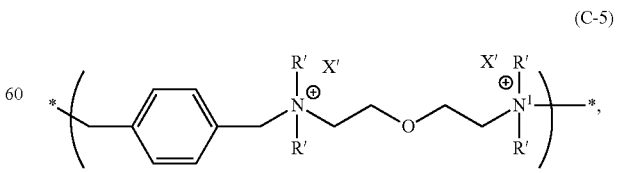

(C-5)

wherein
each R' is an independent monovalent radical selected from the group consisting of methyl, ethyl and propyl, and each X' is an independent negative-charged counterion.

Also disclosed is an antimicrobial composition, comprising an above-described cationic polymer and a second component.

Further disclosed is a method of killing a microbe, comprising contacting the microbe with an above-described cationic polymer.

Also disclosed is a method of forming the cationic polymer of claim 1, comprising:

forming a reaction mixture comprising i) a solvent, ii) an electrophilic agent comprising two leaving groups Y' and an aromatic ring between the two leaving groups, wherein Y' is a leaving group capable of undergoing a nucleophilic substitution reaction with a tertiary amine to form a positive-charged quaternary amine and iii) a nucleophilic agent comprising two tertiary amine groups; and heating the reaction mixture at an elevated temperature with agitation, thereby forming the cationic polymer by addition polymerization of the electrophilic agent and the nucleophilic agent, wherein the cationic polymer is not soluble in the solvent at the elevated temperature.

The above-described and other features and advantages of the present invention will be appreciated and understood by those skilled in the art from the following detailed description, drawings, and appended claims.

DETAILED DESCRIPTION

Figure 1:
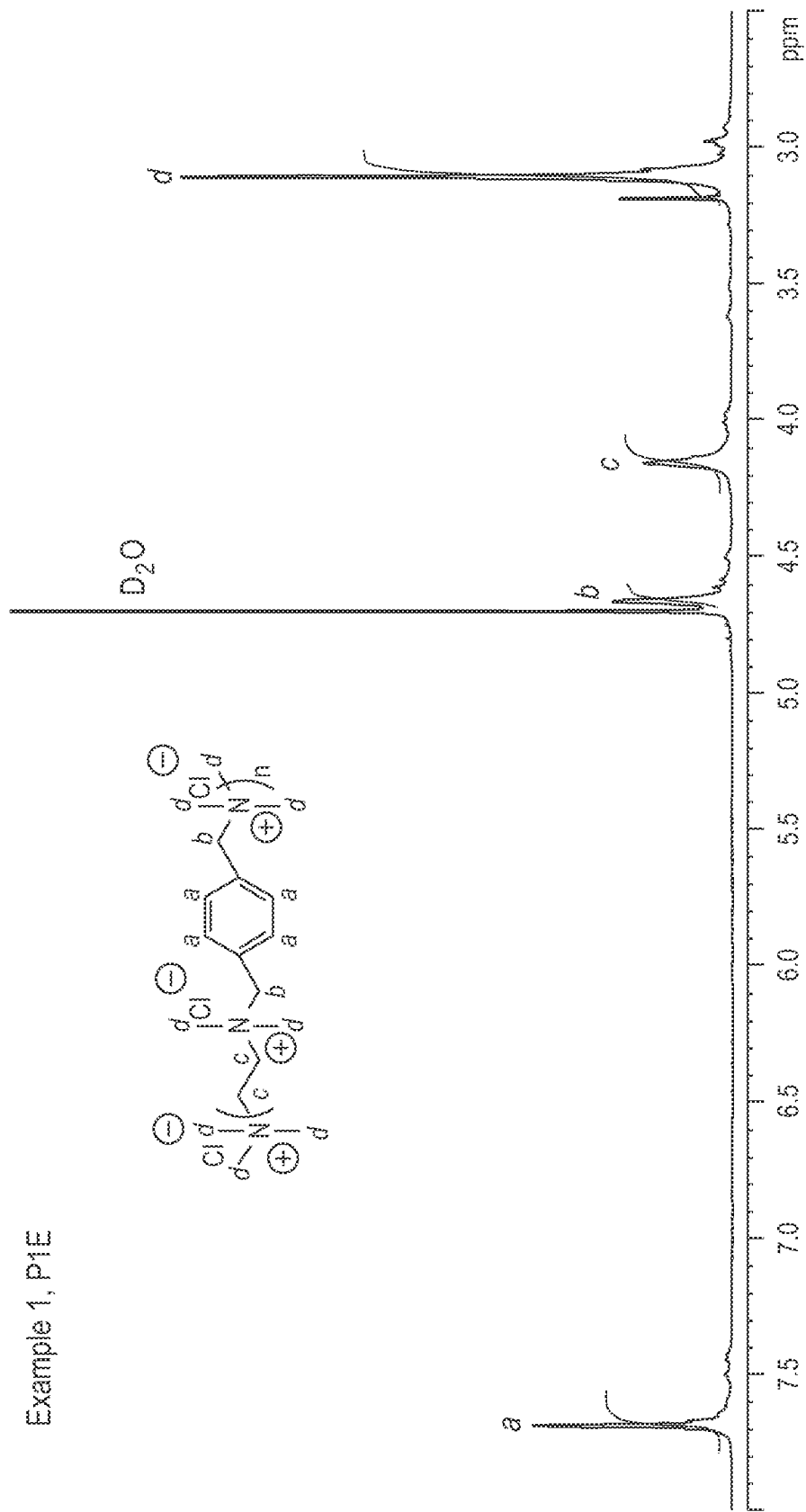
FIG. 1 is a $^1$H NMR spectrum of cationic polymer PIE (Example 1).

Disclosed are antimicrobial cationic polymers that can be formed using a one-step bulk polymerization. The cationic polymers comprise a cationic repeat unit that comprises two positive-charged quaternary nitrogens (i.e., a positive-charged nitrogen covalently bonded only to carbons) and, optionally, one or more oxygen ether groups. The two nitrogens and ether oxygen(s) are also heteroatoms of the polymer backbone. The cationic polymers also comprise divalent hydrocarbon groups that serve as spacer groups for the nitrogen and oxygen heteroatoms of the polymer backbone. The hydrocarbon groups can be aliphatic, cycloaliphatic, aromatic, or a combination thereof. The cationic polymers are stable for several days to aqueous solution of pH 6-7, unlike aliphatic polycarbonates having pendant quaternary amine groups, which can degrade in several days in aqueous solution. The cationic polymers have utility as additives for consumer products (e.g., laundry detergents, hand/body washes, cosmetics, contact lens disinfectants) that require high efficacy against a variety of microbes.

The cationic polymers are represented by the formula (1):

$$E'-P'-E'' \qquad (1)$$

wherein
E' is a first end group,
E'' is a second end group, and
P' is a polymer chain comprising the cationic repeat units.

The cationic polymers are preferably linear polymers. A linear polymer has one branch comprising two peripheral ends, as in a segment of rope. The branch can comprise one or more polymer chain segments joined at respective ends (e.g., as in blocks of a block copolymer linked end to end). P' is preferably a homopolymer or random copolymer comprising one or more of the cationic repeat units.

The cationic repeat unit can have a structure according to formula (C-1):

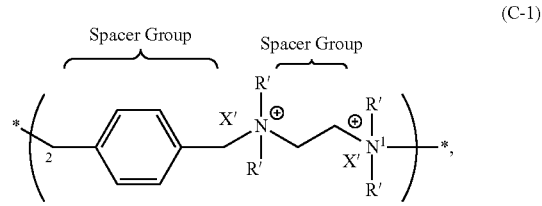

wherein
each X' is an independent negative-charged counterion, and
each R' is an independent monovalent radical selected from the group consisting of methyl, ethyl and propyl.

Herein, a bond with an asterisk is referred to as a "starred bond". A starred bond is not a methyl group. An atomic center shown linked to an asterisk indicates the atomic center is covalently bonded to another atomic center of the chemical structure.

Each X' is bound by ionic association to a positive-charged nitrogen. X' is a free ion, meaning X' is not directly or indirectly covalently linked to the backbone of the cationic polymer. Preferably, each X' in the above structure and those that follow is a halide ion, more specifically chloride ion (Cl⁻), bromide ion (Br⁻), or iodide ion (I⁻).

The cationic repeat units are covalently linked in a head-to-tail arrangement. The nitrogen end of formula (C-1) (i.e., nitrogen 1) is designated the tail, and the carbon end of formula (C-1) (i.e., carbon 2) is designated the head. This convention is followed with other repeat units described below.

A linear homopolymer of formula (C-1) is represented by formula (C-2):

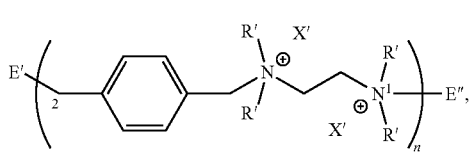

(C-2)

wherein
n represents degree of polymerization (DP), an n has an average value of 5 to 50,
E' is a first end group,
E" is a second end group,
each R' is an independent monovalent radical selected from the group consisting of methyl, ethyl and propyl, and
each X' is an independent negative-charged counterion.

No restriction is placed on end groups E' and E". As non-limiting examples, first end group E' of formula (C-2) can be

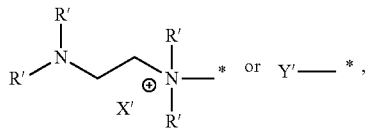

wherein
each R' is an independent monovalent radical selected from the group consisting of methyl, ethyl and propyl,
X' is an independent negative-charged counterion, and
Y' is a leaving group capable of undergoing a nucleophilic substitution reaction with a tertiary amine to form a positive-charged quaternary amine, or a hydrolysis product thereof.

Herein, a tertiary amine comprises a non-charged nitrogen covalently linked only to carbons, preferably three carbons.

As another example, second end group E" of formula (C-2) can be

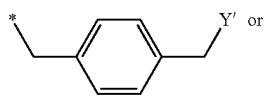

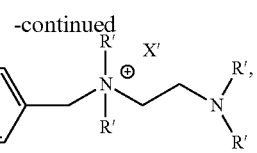

wherein
X' is a negative-charged counterion,
each R' is an independent monovalent radical selected from the group consisting of methyl, ethyl and propyl, and
Y' is a leaving group capable of undergoing a nucleophilic substitution reaction with a tertiary amine to form a positive-charged quaternary amine, or a hydrolysis product thereof.

Other cationic repeat units have a structure according to formula (C-3):

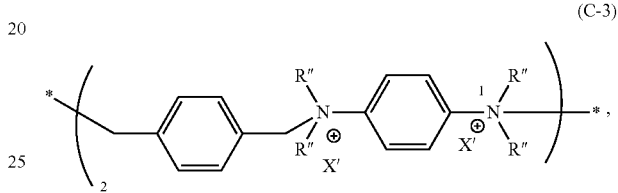

(C-3)

wherein
each X' is an independent negative-charged counterion, and
each R" is an independent monovalent radical selected from the group consisting of methyl, ethyl and propyl.

In formula (C-3), nitrogen 1 is designated the tail, and carbon 2 is designated the head.

A random copolymer of cationic repeat units of formulas (C-1) and (C-3) is represented by formula (C-4):

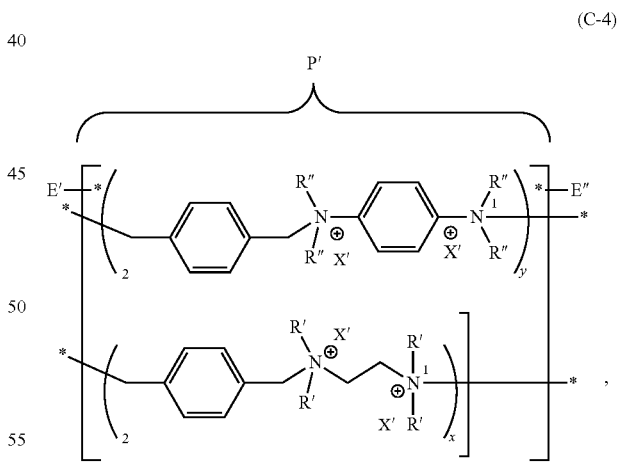

(C-4)

wherein
x represents mole percent (mol %) based on total moles of cationic repeat units of formula (C-1) present in the cationic polymer, and x has a value of 10-90 mol %,
y represents mole percent (mol %) based on total moles of cationic repeat units of formula (C-3) present in the cationic polymer, wherein y has a value of 90-10 mol %,
x+y=100 mol %,
each R' is an independent monovalent radical selected from the group consisting of methyl, ethyl and propyl, each R" is an independent monovalent radical selected from the group consisting of methyl, ethyl and propyl,
E' is a first end group,
E" is a second end group, and
each X' is an independent negative-charged counterion.

In the above notation, polymer chain P' is represented by the parenthesized cationic repeat units enclosed by the square brackets. Vertical stacking of the parenthesized cationic repeat units within the square brackets indicates a random distribution of the cationic repeat units within the P' chain. It should be understood that first end group E' can be linked to carbon 2 of one of the cationic repeat units. Second end group E" can be linked to nitrogen 1 of one of the cationic repeat units. The parenthesized repeat units are linked in a head-to-tail arrangement.

In an embodiment, x is 40-80 mol % and y is 60-20 mol % based on total moles of cationic repeat units present in the cationic polymer of formula (C-4).

Exemplary E' groups of cationic polymers of formula (C-4) include

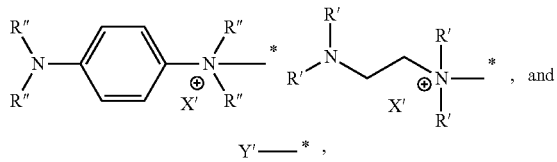

wherein
each R' is an independent monovalent radical selected from the group consisting of methyl, ethyl and propyl,
each R" is an independent monovalent radical selected from the group consisting of methyl, ethyl and propyl,
each X' is an independent negative-charged counterion, and
Y' is a leaving group capable of undergoing a nucleophilic substitution reaction with a tertiary amine to form a positive-charged quaternary amine, or a hydrolysis product thereof.

Preferably, Y' is a halide selected from the group consisting of chloride (Cl—*), bromide (Br—*), and iodide (I—*).

Exemplary E' groups of cationic polymers of formula (C-4) include

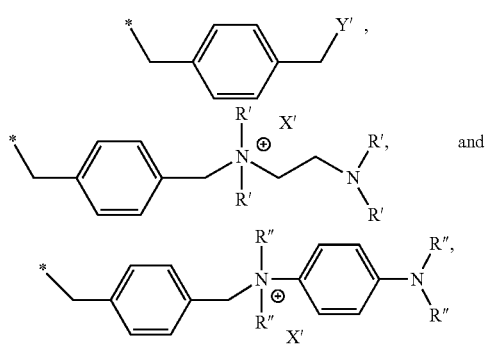

wherein
each R' is an independent monovalent radical selected from the group consisting of methyl, ethyl and propyl,
each R" is an independent monovalent radical selected from the group consisting of methyl, ethyl and propyl,
each X' is an independent negative-charged counterion, and
Y' is a leaving group capable of undergoing a nucleophilic substitution reaction with a tertiary amine to form a positive-charged quaternary amine, or a hydrolysis product thereof.

In an embodiment, each R' is methyl and each R" is methyl.

Other cationic repeat units have formula (C-5):

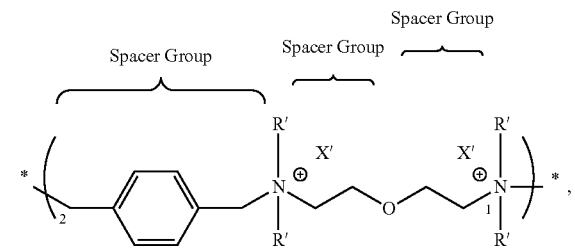

wherein
each R' is an independent monovalent radical selected from the group consisting of methyl, ethyl and propyl, and
each X' is an independent negative-charged counterion.

A linear homopolymer comprising cationic repeat units of formula (C-5) is represented by formula (C-6):

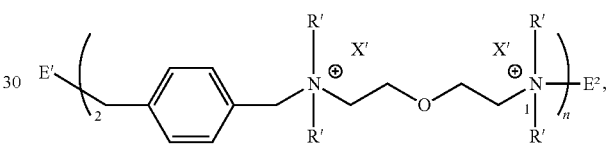

wherein
n represents degree of polymerization (DP), and n has an average value of 5 to 50,
E' is a first end group,
E" is a second end group,
each R' is an independent monovalent radical selected from the group consisting of methyl, ethyl and propyl, and
each X' is an independent negative-charged counterion.

Exemplary, non-limiting E' groups of formula (C-6) include

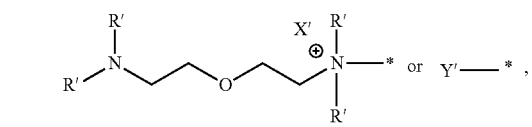

wherein
each R' is an independent monovalent radical selected from the group consisting of methyl, ethyl and propyl,
X' is an independent negative-charged counterion, and
Y' is a leaving group capable of undergoing a nucleophilic substitution reaction with a tertiary amine to form a positive-charged quaternary amine, or a hydrolysis product thereof.

Exemplary, non-limiting E" groups of formula (C-6) include

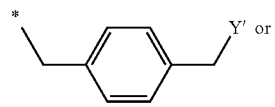

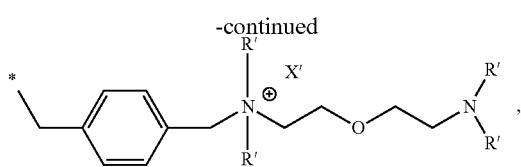

wherein

X' is an independent negative-charged counterion, each R' is an independent monovalent radical selected from the group consisting of methyl, ethyl and propyl, and Y' is a leaving group capable of undergoing a nucleophilic substitution reaction with a tertiary amine to form a positive-charged quaternary amine, or a hydrolysis product thereof.

Other cationic repeat units have a structure according to formula (C-7):

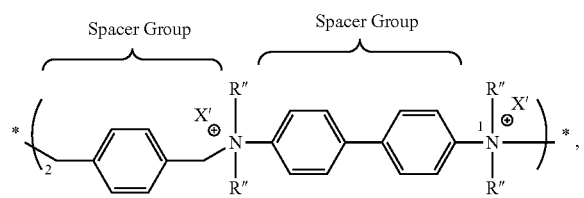

(C-7)

wherein each X' is an independent negative-charged counterion, and each R'' is an independent monovalent radical selected from the group consisting of methyl, ethyl and propyl.

In formula (C-7), nitrogen 1 is designated the tail, and carbon 2 is designated the head.

In an embodiment, the cationic copolymer is a random copolymer represented by formula (C-8):

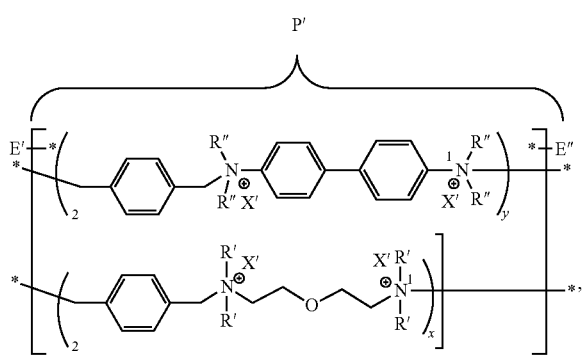

(C-8)

wherein x represents mole percent (mol %) based on total moles of cationic repeat units present in the cationic polymer, and x has a value of 10-90 mol %, y represents mole percent (mol %) based on total moles of cationic repeat units present in the cationic polymer, and y has a value of 90-10 mol %, each R' is an independent monovalent radical selected from the group consisting of methyl, ethyl and propyl, each R'' is an independent monovalent radical selected from the group consisting of methyl, ethyl and propyl, E' is a first end group, E'' is a second end group, and each X' is an independent negative-charged counterion.

First end group E' can be linked to carbon 2 of one of the cationic repeat units within the square brackets. Second end group E'' can be linked to nitrogen 1 of one of cationic repeat units within the square brackets.

In an embodiment, x is 40-80 mol % and y is 60-20 mol % based on total moles of cationic repeat units present in the cationic polymer.

Exemplary, non-limiting E' groups of formula (C-8) include

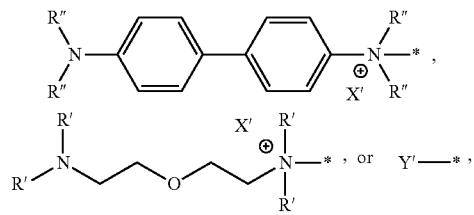

wherein each R' is an independent monovalent radical selected from the group consisting of methyl, ethyl and propyl, each R'' is an independent monovalent radical selected from the group consisting of methyl, ethyl and propyl, each X' is an independent negative-charged counterion, and Y' is a leaving group capable of undergoing a nucleophilic substitution reaction with a tertiary amine to form a positive-charged quaternary amine, or a hydrolysis product thereof.

Preferably, Y' is a halide selected from the group consisting of chloride (Cl—*), bromide (Br—*), and iodide (I—*).

Exemplary, non-limiting E'' groups of formula (C-8) include

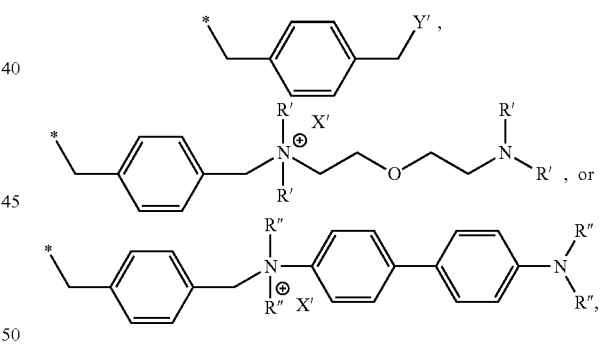

wherein each R' is an independent monovalent radical selected from the group consisting of methyl, ethyl and propyl, each R'' is an independent monovalent radical selected from the group consisting of methyl, ethyl and propyl, each X' is an independent negative-charged counterion, and Y' is a leaving group capable of undergoing a nucleophilic substitution reaction with a tertiary amine to form a positive-charged quaternary amine, or a hydrolysis product thereof.

In an embodiment, each R' and R'' of cationic polymers of formula (C-8) is methyl.

The cationic polymers can be synthesized by a bulk addition polymerization reaction without employing a separate catalyst. The quaternization reaction and polymerization are accomplished concurrently. In a preferred method of forming the cationic polymers, a reaction mixture is prepared comprising a solvent, an electrophilic agent comprising two leaving groups, and a nucleophilic agent comprising two tertiary amine groups. The electrophilic agent preferably comprises an aromatic ring between the two leaving groups. The leaving groups (e.g., halide, mesylate, tosylate groups) are independently capable of being displaced by a tertiary amine in a nucleophilic substitution reaction, thereby forming a quaternary amine. The quaternary amine comprises a positive-charged nitrogen covalently bonded only to carbons, preferably 4 carbons. Heating the reaction mixture to a suitable temperature dissolves the reactants and initiates polymerization. The polymerization conditions are selected in order to terminate chain growth using a diffusion limited mechanism (e.g., by using a solvent that allows the polymer to precipitate from solution at elevated temperature after achieving a threshold molecular weight). Using this technique, cationic polymers of modest molecular weight are formed that have desirable antimicrobial activity, and are non-hemolytic and non-cytotoxic. A preferred solvent for this purpose is dimethylformamide (DMF), which dissolves the reactants at elevated temperatures and allows the product cationic polymers to precipitate from solution at the polymerization temperature. In this manner, the homopolymers and random copolymers can be prepared in one step.

The cationic polymers can have a number average molecular weight (Mn) of about 1000 to 10000, more specifically, 3000 to 8000. The cationic polymers can have a polydispersity index (PDI) of 1.0 to 5.0, more specifically 1.0 to 3.0, and even more specifically, 1.0 to 2.0.

Non-limiting electrophilic agents include the following materials.

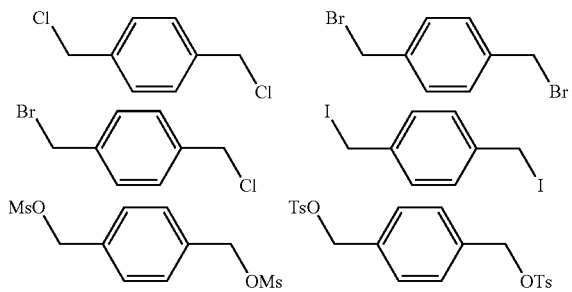

Non-limiting nucleophilic agents include the following di-tertiaryamines.

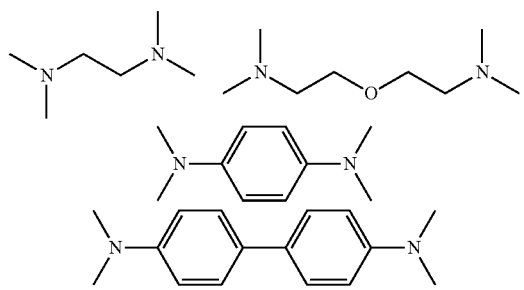

Antimicrobial Properties

The following definitions are applicable.

HC50 is defined as the concentration (in mg/L) of cationic polymer that causes 50% of mammalian red blood cells to undergo hemolysis. HC50 values of 1000 mg/L or higher are desirable.

HC20 is defined as the concentration (in mg/L) of cationic polymer that causes 20% of mammalian red blood cells to undergo hemolysis. HC20 values of 500 mg/L or higher are desirable.

Minimum inhibitory concentration (MIC) is defined as the minimum concentration (in mg/L) of cationic polymer required to inhibit growth of a given microbe for an 18 hour period (bacteria) or 42 hour period (fungi). A MIC less than 500 mg/L is desirable. Even more desirable is a MIC of 150 mg/L or less. A lower MIC indicates higher antimicrobial activity.

Minimum bactericidal concentration (MBC) is defined as the minimum concentration (in mg/L) of cationic polymer required to kill a given microbe. A lower MBC indicates higher antimicrobial activity.

HC50 selectivity is defined as the ratio of HC50/MIC. An HC50 selectivity of 3 or more is desirable. Higher HC50 selectivity values indicate more activity against bacterial cells and less toxicity to mammalian cells. Likewise, HC20 selectivity is defined as the ratio of HC20/MIC. An HC20 selectivity of 3 or more is desirable.

Non-limiting exemplary bacteria include Gram-positive *Staphylococcus aureus* (*S. aureus*), Gram-negative *Escherichia coli* (*E. coli*), fungus *Candida albicans* (*C. albicans*), Gram-negative *Pseudomonas aeruginosa* (*P. aeruginosa*), and yeasts. Other microbes include Gram-positive *Staphylococcus epidermidis* (*S. epidermidis*), Gram-positive Methicillin-resistant *Staphylococcus aureus* (MRSA), Gram-positive Vancomycin-resistant *Enterococcus* (VRE), Gram-negative *Acinetobacter baumannii* (*A. baumannii*), and Gram-negative *Klebsiella pneumoniae* (*K. pneumoniae*) and *Cryptococcus neoformans* (*C. neoformans*).

The cationic polymers can have a minimum inhibitory concentration (MIC) of about 1 mg/L to about 500 mg/L, and more preferably about 1 mg/L to about 250 mg/L, and most preferably 1 mg/L to about 125 mg/L against a bacterium. In an embodiment, the cationic polymers have a MIC of about 1 mg/L to about 10 mg/L against *P. aeruginosa*.

The cationic polymers can exhibit less than about 50% hemolysis at 1000 mg/L (i.e., can have an HC50 value greater than 1000 mg/L).

INDUSTRIAL APPLICABILITY

The cationic polymers have utility as antimicrobial components of consumer products that are used in contact with skin such as, for example, cosmetics (e.g., skin lotions, skin creams, topically applied powders, mascara, eye liners, lip glosses), soaps, shampoos, and deodorants. The cationic polymers also have utility as antimicrobial components of laundry detergents.

The cationic polymers also have utility for human and/or non-human therapeutic medical treatments. The polymers can be used in the form of a stand-alone antibiotic drug and/or as a complex comprising the cationic polymer and an anionic form of biologically active material (e.g., genes, drugs) bound by non-covalent interactions. A medical composition comprising the cationic polymer and/or a biologically active material selected from the group consisting of genes, drugs, and combinations thereof, can be administered topically, intravenously, orally, by way of other body cavities, and/or by inhalant. The medical composition can have the form of a powder, a pill, a liquid, a paste, or a gel. The medical compositions are particularly attractive for use in injectable systems for delivery of rigid, hydrophobic biologically active materials that have low water solubility, such as the drugs paclitaxel and doxorubicin.

A method comprises contacting a microbe with a cationic polymer, thereby killing the microbe.

Another method comprises contacting a tumor cell with a complex comprising a disclosed cationic polymer and a tumor-treating drug, thereby killing the tumor cell.

Antimicrobial compositions are disclosed that comprise a cationic polymer and at least one other component (e.g., water, drug, gene). The antimicrobial composition can be applied to a human and/or non-human animal tissue, including mammalian and/or non-mammalian animal tissue. The general term "animal tissue" includes wound tissue, burn tissue, skin, internal organ tissue, blood, bones, cartilage, teeth, hair, eyes, nasal surfaces, oral surfaces, other body cavity surfaces, and any cell membrane surfaces. In an embodiment, a method comprises contacting an animal tissue with the antimicrobial composition, thereby inhibiting, preventing, and/or eradicating a microbial infection of the tissue.

Other uses of the cationic polymers include disinfectant washes for hands, skin, hair, bone, ear, eye, nose, throat, internal tissue, wounds, and teeth (e.g., as a mouthwash).

Still other uses of the cationic polymers include disinfectants for articles such as medical devices. Medical devices include swabs, catheters, sutures, stents, bedpans, gloves, facial masks, absorbent pads, absorbent garments, internal absorbent devices, and insertable mechanical devices. In an embodiment, a method comprises contacting a medical device with an antimicrobial composition comprising a disclosed cationic polymer, thereby disinfecting the medical device. In an embodiment, the medical device is a catheter.

The antimicrobial compositions are also attractive as disinfecting agents for surfaces of articles (i.e., non-living articles) such as, for example, building surfaces in homes, businesses, and particularly hospitals. Exemplary home and commercial building surfaces include floors, door surfaces, bed surfaces, air conditioning surfaces, bathroom surfaces, railing surfaces, kitchen surfaces, and wall surfaces. Other articles include medical devices, cloths, garments, and non-medical equipment. Surfaces of articles can comprise materials such as wood, paper, metal, cloth, plastic, rubber, glass, paint, leather, or combinations thereof. In an embodiment, a method comprises contacting a surface of an article with an antimicrobial composition comprising a disclosed cationic polymer, thereby disinfecting the surface. In another embodiment, the antimicrobial composition has the form of a solution.

In an embodiment, the antimicrobial composition is selected from the group consisting of soaps, shampoos, skin lotions, skin creams, cosmetics, mouthwashes, wound care agents, deodorants, surface cleaning agents, and laundry detergents.

Loaded Complexes

In water, optionally containing organic solvent, the cationic polymers can form a nanoparticulate complex with an anionic biologically active cargo material, bound by non-covalent interactions. These "loaded" complexes can have the form of a micelle that comprises a plurality of self-assembled macromolecules of the cationic polymer and one or more molecules of the cargo material encapsulated therein.

A method of forming a nanoparticulate loaded complex comprises i) forming a first solution comprising a cationic polymer (i.e., carrier) and water; ii) forming a second solution comprising a biologically active material (i.e., cargo) in water and/or a water miscible organic solvent; iii) combining the first and seconds solutions; and iv) removing any organic solvent (e.g., by dialysis), thereby forming an aqueous mixture comprising the loaded complex. The complex can comprise the cationic polymer in an amount of 85.0 wt. % to 99.9 wt. %, and the biologically active material in an amount of about 15.0 wt. % to 0.1 wt. %, each based on total dry solids weight of the loaded complex.

The term "loading efficiency" refers to the percentage of the initial weight of the biologically active material that is incorporated into the loaded complex. The loading efficiency of the biologically active material in the loaded complex is preferably at least 10%. Generally, the loading efficiency of the biologically active material is in a range of 10% to 50%, and even more specifically in a range of 30% to 50%.

Nanoparticles of the loaded complex can have an average particle size (circular cross sectional diameter) of 10 nm to 500 nm, 10 nm to 250 nm, and preferably 25 nm to 200 nm as measured by dynamic light scattering. For the foregoing particle sizes, the aqueous solution can have a pH of 4.5 to 8.0, 5.0 to 7.0, or 6.0 to 7.0.

The organic solvent, if any, used to prepare the loaded complex is preferably miscible with water at concentrations of at least 1 microliter or more of organic solvent per 100 microliters of water. Exemplary organic solvents include methanol, ethanol, propanol, 2-propanol, 1-butanol, 2-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, dimethylformamide, acetic acid, tetrahydrofuran (THF), and dioxane.

As stated above, the biologically active cargo material can be a drug. Exemplary commercially available drugs include the following, where the generic drug is enclosed in parentheses next to the all-capitalized registered trade name: 13-cis-Retinoic Acid, 2-CdA (Cladribine), 2-Chlorodeoxyadenosine (Cladribine), 5-Azacitidine, 5-Fluorouracil (Fluorouracil), 5-FU (Fluorouracil), 6-Mercaptopurine, 6-MP (6-Mercaptopurine), 6-TG (Thioguanine), 6-Thioguanine (Thioguanine), ABRAXANE® (Paclitaxel protein bound), ACCUTANE® (Isotretinoin), Actinomycin-D (Dactinomycin), ADRIAMYCIN® (Doxorubicin), ADRUCIL® (Fluorouracil), AFINITOR® (Everolimus), AGRYLIN® (Anagrelide), ALA-CORT® (Hydrocortisone), Aldesleukin, Alemtuzumab, ALIMTA® (Pemetrexed), Alitretinoin (9-cis-retinoic acid), Alkaban-AQ (Vinblastine), ALKERAN® (Melphalan), All-transretinoic Acid (Tretinoin), Alpha Interferon (Interferon Alfa), Altretamine, Amethopterin (Methotrexate), Amifostine, Aminoglutethimide, Anagrelide, ANANDRON® (Nilutamide), Anastrozole, Arabinosylcytosine (Cytarabine), Ara-C (Cytarabine), ARANESP® (Darbepoetin Alfa), AREDIA® (Pamidronate), ARIMIDEX® (Anastrozole), AROMASIN® (Exemestane), ARRANON® (Nelarabine), Arsenic Trioxide, Asparaginase, ATRA (All-transretinoic Acid), AVASTIN® (Bevacizumab), Azacitidine, BCG, BCNU (Carmustine), Bendamustine (Bendamustine Hydrochloride), Bevacizumab, Bexarotene, BEXXAR® (Tositumomab), Bicalutamide, BICNU® (Carmustine), BLENOXANE® (Bleomycin), Bleomycin, Bortezomib, Busulfan, BUSULFEX® (Busulfan), C225 (Cetuximab), Calcium Leucovorin (Leucovorin), CAMPATH® (Alemtuzumab), CAMPTOSAR® (Irinotecan), Camptothecin-11 (Irinotecan), Capecitabine, CARAC® (Fluorouracil), Carboplatin, Carmustine, Carmustine Wafer, CASODEX® (Bicalutamide), CC-5013 (Lenalidomide), CCI-779 (Temsirolimus), CCNU (Lomustine), CDDP (Cisplatin), CEENU® (Lomustine), CERUBIDINE® (Daunomycin), Cetuximab, Chlorambucil, Cisplatin, Citrovorum Factor (Leucovorin), Cladribine, Cortisone (Hydrocortisone), COSMOGEN® (Dactinomycin), CPT-11 (Irinotecan), Cyclophosphamide, CYTADREN® (Aminoglutethimide), Cytarabine, Cytarabine Liposomal, CYTOSAR-U® (Cytarabine), CYTOXAN® (Cyclophosphamide), Dacarbazine, DACOGEN® (Decitabine), Dactinomycin, Darbepoetin Alfa, Dasatinib, Daunomycin, Daunorubicin, Daunorubicin Hydrochloride, Daunorubicin Liposomal, DAUNOXOME® (Daunorubicin Liposomal), DECADRON™ (Dexamethasone), Decitabine, DELTA-CORTEF® (Prednisolone), DELTASONE® (Prednisone), Denileukin Diftitox, DEPOCYT® (Cytarabine Liposomal), Dexamethasone, Dexamethasone Acetate, Dexamethasone Sodium Phosphate, DEXASONE® (Dexamethasone), Dexrazoxane, DHAD (Mitoxantrone), DIC (Dacarbazine), DIODEX® (Dexamethasone), Docetaxel, DOXIL® (Doxorubicin Liposomal), Doxorubicin, Doxorubicin Liposomal, DROXIA® (Hydroxyurea), DTIC (Dacarbazine), DTIC-DOME® (Decarbazine), Duralone (Methylprednisolone), EFUDEX® (Fluorouracil), ELIGARD® (Leuprolide), ELLENCE® (Epirubicin), ELOXATIN® (Oxaliplatin), ELSPAR® (Asparaginase), EMCYT® (Estramustine), Epirubicin, Epoetin Alfa, ERBITUX® (Cetuximab), Erlotinib, *Erwinia* L-asparaginase (Asparaginase), Estramustine, ETHYOL® (Amifostine), ETOPOPHOS® (Etoposide), Etoposide, Etoposide Phosphate, EULEXIN® (Flutamide), Everolimus, EVISTA® (Raloxifene), Exemestane, FARESTON® (Toremifene), FASLODEX® (Fulvestrant), FEMARA® (Letrozole), Filgrastim, Floxuridine, FLUDARA® (Fludarabine), Fludarabine, FLUOROPLE® (Fluorouracil), Fluorouracil, Fluorouracil (cream), Fluoxymesterone, Flutamide, Folinic Acid (Leucovorin), FUDR® (Floxuridine), Fulvestrant, G-CSF (Pegfilgrastim), Gefitinib, Gemcitabine, Gemtuzumab ozogamicin, GEMZAR® (Gemcitabine), GLEEVEC® (Imatinib mesylate), GLIADEL® Wafer (Carmustine Wafer), GM-CSF (Sargramostim), Goserelin, Granulocyte-Colony Stimulating Factor (Pegfilgrastim), Granulocyte Macrophage Colony Stimulating Factor (Sargramostim), HALOTESTIN® (Fluoxymesterone), HERCEPTIN® (Trastuzumab), HEXADROL® (Dexamethasone), HEXALEN® (Altretamine), Hexamethylmelamine (Altretamine), HMM (Altretamine), HYCAMTIN® (Topotecan), HYDREA® (Hydroxyurea), Hydrocort Acetate (Hydrocortisone), Hydrocortisone, Hydrocortisone Sodium Phosphate, Hydrocortisone Sodium Succinate, HYDROCORTONE® Phosphate (Hydrocortisone), Hydroxyurea, Ibritumomab, Ibritumomab Tiuxetan (Ibritumomab), IDAMYCIN® (Idarubicin), Idarubicin, IFEX® (Ifosfamide), IFN-alpha (Interferon alfa), Ifosfamide, IL-11 (Oprelvekin), IL-2 (Aldesleukin), Imatinib mesylate, Imidazole Carboxamide (Decarbazine), Interferon alfa, Interferon Alfa-2b (PEG Conjugate), Interleukin-2 (Aldesleukin), Interleukin-11 (Oprelvekin), INTRON® A (interferon alfa-2b), IRESSA® (Gefitinib), Irinotecan, Isotretinoin, Ixabepilone, IXEMPRA® (Ixabepilone), Kidrolase (Asparaginase), LANACORT® (Hydrocortisone), Lapatinib, L-asparaginase, LCR (Vincristine), Lenalidomide, Letrozole, Leucovorin, LEUKERAN® (Chlorambucil), LEUKINE® (Sargramostim), Leuprolide, Leurocristine (Vincristine), LEUSTATIN® (Cladribine), Liposomal Ara-C, LIQUID PRED® (Prednisone), Lomustine, L-PAM (Melphalen), L-Sarcolysin (Melphalen), LUPRON® (Leuprolide), LUPRON DEPOT® (Leuprolide), MATULANE® (Procarbazine), MAXIDEX® (Dexamethasone), Mechlorethamine, Mechlorethamine Hydrochloride, Medralone (Methylprednisolone), MEDROL® (Methylprednisolone), MEGACE® (Megestrol), Megestrol, Megestrol Acetate (Megastrol), Melphalan, Mercaptopurine (6-Mercaptopurine), Mesna, MESNEX® (Mesna), Methotrexate, Methotrexate Sodium (Methotrexate), Methylprednisolone, METICORTEN® (Prednisone), Mitomycin (Mitomycin C), Mitomycin-C, Mitoxantrone, M-Prednisol (Methylprednisolone), MTC (Mitomycin-C), MTX (Methotrexate), MUSTARGEN® (Mechlorethamine), Mustine (Mechlorethamine), MUTAMYCIN® (Mitomycin-C), MYLERAN® (Busulfan), MYLOCEL® (Hydroxyurea), MYLOTARG® (Gemtuzumab ozogamicin), NAVELBINE® (Vinorelbine), Nelarabine, NEOSAR® (Cyclophosphamide), NEULASTA® (Pegfilgrastim), NEUMEGA® (Oprelvekin), NEUPOGEN® (Filgrastim), NEXAVAR® (Sorafenib), NILANDRON® (Nilutamide), Nilutamide, NIPENT® (Pentostatin), Nitrogen Mustard (Mechlorethamine), NOLVADEX® (Tamoxifen), NOVANTRONE® (Mitoxantrone), Octreotide, Octreotide acetate (Octreotide), ONCASPAR® (Pegaspargase), ONCOVIN® (Vincristine), ONTAK® (Denileukin Diftitox), ONXOL® (Paclitaxel), Oprelvekin (Interleukin-11), ORAPRED® (Prednisolone), ORASONE® (Prednisone), Oxaliplatin, Paclitaxel, Paclitaxel Protein-bound, Pamidronate, Panitumumab, PANRETIN® (Alitretinoin), PARAPLATIN® (Carboplatin), PEDIAPRED® (Prednisolone), PEG Interferon, Pegaspargase, Pegfilgrastim, PEG-INTRON® (Interferon Alfa-2b), PEG-L-asparaginase, Pemetrexed, Pentostatin, Phenylalanine Mustard (Melphalen), PLATINOL® (Cisplatin), Platinol-AQ (Cisplatin), Prednisolone, Prednisone, PRELONE® (Prednisolone), Procarbazine, PROCRIT® (Epoetin Alfa), PROLEUKIN® (Aldesleukin), Prolifeprospan 20 with Carmustine Implant (Carmustine Wafer), PURINETHOL® (6-Mercaptopurine), Raloxifene, REVLIMID® (Lenalidomide), RHEUMATREX® (Methotrexate), RITUXAN® (Rituximab), Rituximab, Roferon-A (Interferon Alfa-2a), RUBEX® (Doxorubicin), Rubidomycin hydrochloride (Daunomycin), SANDOSTATIN® (Octreotide), SANDOSTATIN LAR® (Octreotide), Sargramostim, SOLU-CORTEF® (Hydrocortisone), SOLU-MEDROL® (Methylprednisolone), Sorafenib, SPRYCEL® (Dasatinib), STI-571 (Imatinib Mesylate), Streptozocin, SU11248 (Sunitinib), Sunitinib, SUTENT® (Sunitinib), Tamoxifen, TARCEVA® (Erlotinib), TARGRETIN® (Bexarotene), TAXOL® (Paclitaxel), TAXOTERE® (Docetaxel), TEMODAR® (Temozolomide), Temozolomide, Temsirolimus, Teniposide, TESPA (Thiotepa), Thalidomide, THALOMID® (Thalidomide), THERACYS® (BCG), Thioguanine, Thioguanine Tabloid (Thioguanine), Thiophosphoamide (Thiotepa), THIOPLEX® (Thiotepa), Thiotepa, TICE® (BCG), TOPOSAR® (Etoposide), Topotecan, Toremifene, TORISEL® (Temsirolimus), Tositumomab, Trastuzumab, TREANDA® (Bendamustine Hydrochloride), Tretinoin, TREXALL® (Methotrexate), TRISENOX® (Arsenic Trioxide), TSPA (Thiotepa), TYKERB® (Lapatinib), VCR (Vincristine), VECTIBIX® (Panitumumab), VELBAN® (Vinblastine), VELCADE® (Bortezomib), VEPESID® (Etoposide), VESANOID® (Tretinoin), VIADUR® (Leuprolide), VIDAZA® (Azacitidine), Vinblastine, Vinblastine Sulfate, VINCASAR PFS® (Vincristine), Vincristine, Vinorelbine, Vinorelbine tartrate (Vinorelbine), VLB (Vinblastine), VM-26 (Teniposide), Vorinostat, VP-16 (Etoposide), VUMON® (Teniposide), XELODA® (Capecitabine), ZANOSAR® (Streptozocin), ZEVALIN® (Ibritumomab), ZINECARD® (Dexrazoxane), ZOLADEX® (Goserelin), Zoledronic acid, ZOLINZA® (Vorinostat), and ZOMETA® (Zoledronic acid).

The following examples demonstrate the preparation, antimicrobial properties, hemolytic properties, and cytotoxicity of the cationic polymers.

Examples

Materials used in the following examples are listed in Table 1.

TABLE 1

| ABBREVIATION | DESCRIPTION | SUPPLIER |
|---|---|---|
| DCMB | 1,4-Bis(chloromethyl)benzene | Sigma-Aldrich |
| DHPAE | N,N,N',N'-Tetrakis(2-hydroxypropan-1-yl)ethylenediamine | Sigma-Aldrich |
| DMAB | 1,4-N,N-Dimethylaminobenzene | Sigma-Aldrich |
| DMABP | 4,4'-Dimethylamino-1,1-biphenyl | Sigma-Aldrich |
| DMAE | 1,2-Dimethylaminoethane | Sigma-Aldrich |
| DMAEE | 2,2'-Dimethylaminoethyl ether | Sigma-Aldrich |
| DMEM | Dulbecco's Modified Eagle Medium | Invitrogen |
| DMF | N,N-Dimethylformamide | Sigma-Aldrich |
| FBS | Fetal Bovine Serum | Invitrogen |
| HDF | Human dermal fibroblasts | ATCC, USA |
| MHB | Mueller Hinton Broth | BD Diagnostics, SG |
| MTT | 3-[4,5-Dimenthylthiazol-2-yl]-2,5-diphenyl tetrazolium bromide | Invitrogen |
| PBS | Phosphate Buffered Saline | 1$^{st}$ Base, SG |
| TSB | Tryptic Soy Broth | BD Diagnostics, SG |
| YMB | Yeast Mold Broth | BD Diagnostics, SG |

Herein, Mn is the number average molecular weight, Mw is the weight average molecular weight, and MW is the molecular weight of one molecule.

All chemical reagents were purchased from Sigma-Aldrich, U.S.A. and used as received unless specified. Muller Hinton Broth (MHB) powder was purchased from BD Diagnostics (Singapore) and used to prepare the microbial broths according to the manufacturer's instruction. Cell lines of human dermal fibroblasts (HDF), *Staphylococus aureus* (ATCC No. 6538), *Escherichia coli* (ATCC No. 25922), *Pseudomonas aeruginosa* (ATCC No. 9027), and *Candida albicans* (ATCC No 10231) were obtained from ATCC, U.S.A., and reconstituted according to the suggested protocols. Fetal bovine serum was purchased from Invitrogen Corporation. 3-[4,5-Dimenthylthiazol-2-yl]-2,5-diphenyl tetrazolium bromide (MTT) was dissolved in phosphate-buffered saline (PBS, pH 7.4) with a concentration of 5 mg/mL, and the solution was filtered with a 0.22 μm filter to remove blue formazan crystals prior to usage. Rat red blood cells (RBCs) were obtained from the Animal Handling Unit of Biomedical Research Centers (Singapore).

Weight average molecular weights (Mw) of the polymers were determined by a Waters gel permeation chromatography ((Waters 2695, MA, USA) system with two ultrahydrogel columns (Waters, size: 300×7.8 mm) in series with a differential refractometer detector (Waters 2414, MA, USA). The mobile phase used was water containing 0.1M trifluoroacetic acid (TFA) with a flow rate of 0.5 mL/min. Weight average molecular weights as well as polydispersity indices were calculated from a calibration curve using a series of poly(ethylene glycol) standards (Polymer Standard Service Inc., RI, USA, with molecular weights ranging from 633 to 20,600).

The commercially available dihalide monomer DCMB was used in the preparations that follow.

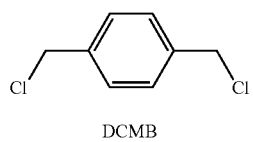

DCMB

The following commercially available diamine monomers were used in the preparations that follow.

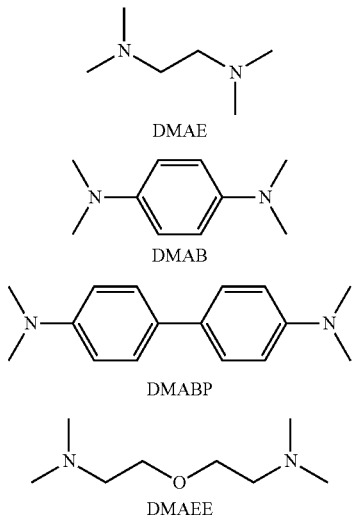

Polymer Preparations

Example 1. Preparation of Cationic Homopolymer P1E

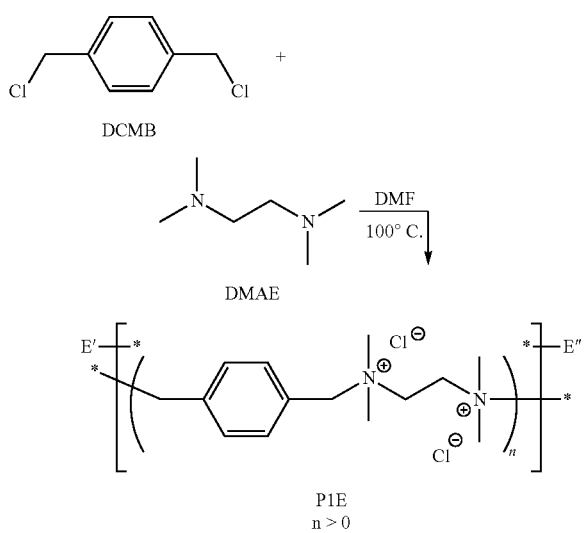

P1E
n > 0

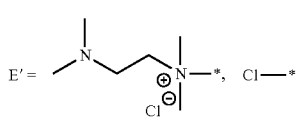

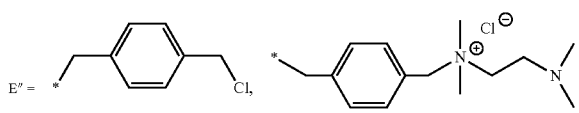

Possible end groups E' and E" are listed above for a given macromolecule of homopolymer P1E. Homopolymer P1E can also be written as follows.

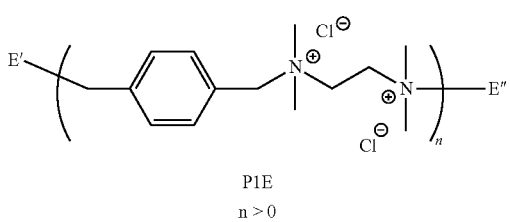

P1E
n > 0

The following procedure is representative. To a round bottom flask equipped with a nitrogen inlet was added DCMB (1.01 g, 5.76 mmol) and DMF (20 mL). A solution of DMAE (0.669 g, 5.76 mmol) in DMF (20 mL) was then added dropwise over 0.5 h at room temperature. The reaction is exothermic. After the addition was complete, the reaction mixture was heated to 100° C. and stirred for 18 hours, resulting in a precipitate. The polymer was isolated by filtration and washed with ethyl ether (3×50 mL) to afford a white powder in near quantitative yield. FIG. 1 is a $^1$H NMR spectrum of P1E.

Example 2. Preparation of Cationic Polymer P1B

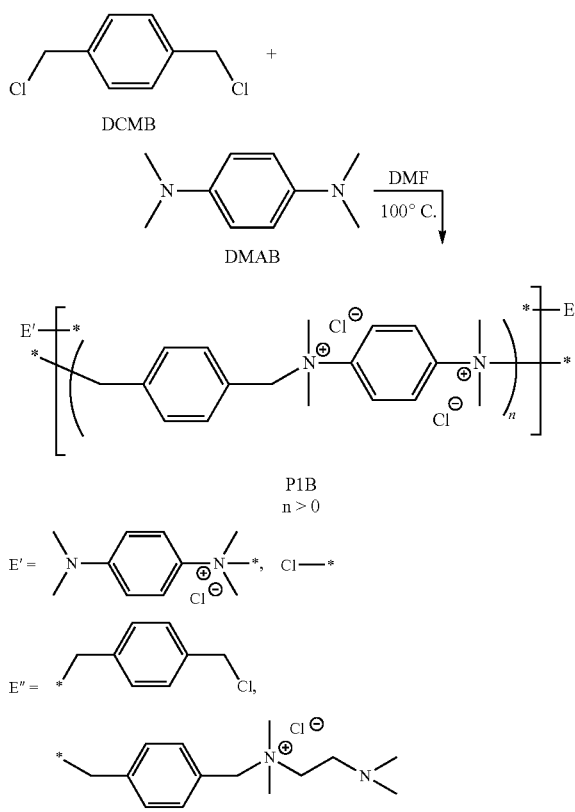

Figure 2:
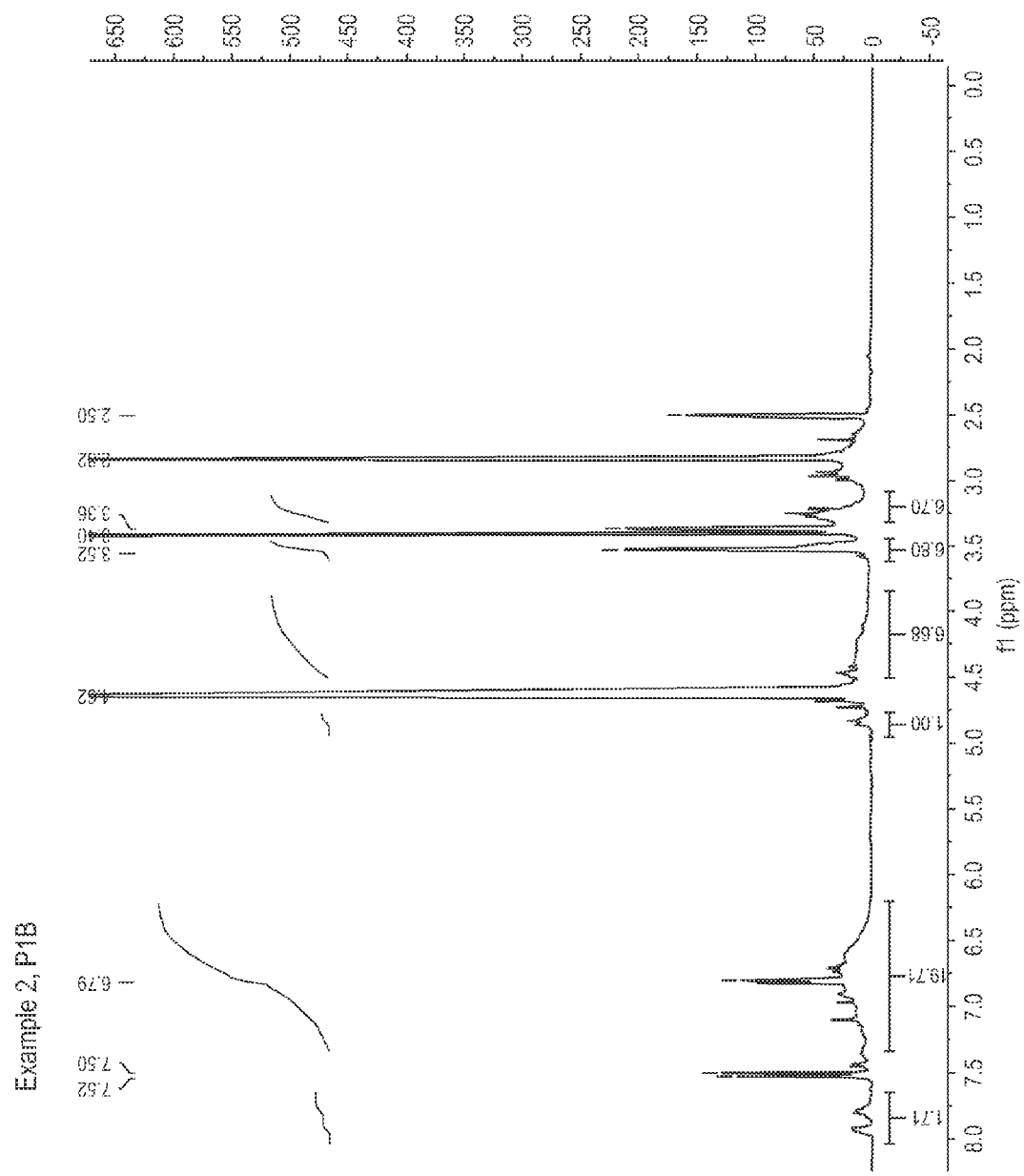
FIG. 2 is a $^1$H NMR spectrum of cationic polymer PIB (Example 2).

Possible end groups E' and E" are listed above for a given macromolecule of cationic homopolymer P1B (n>0). P1B was prepared according to the general procedure of Example 1 using DCMB (0.974 g, 5.50 mmol) and DMAB (0.915 g, 5.50 mmol, 1 eq.) and isolated in near quantitative yield. FIG. 2 is a $^1$H NMR spectrum of P1B.

Example 3. Preparation of Cationic Homopolymer P1EE

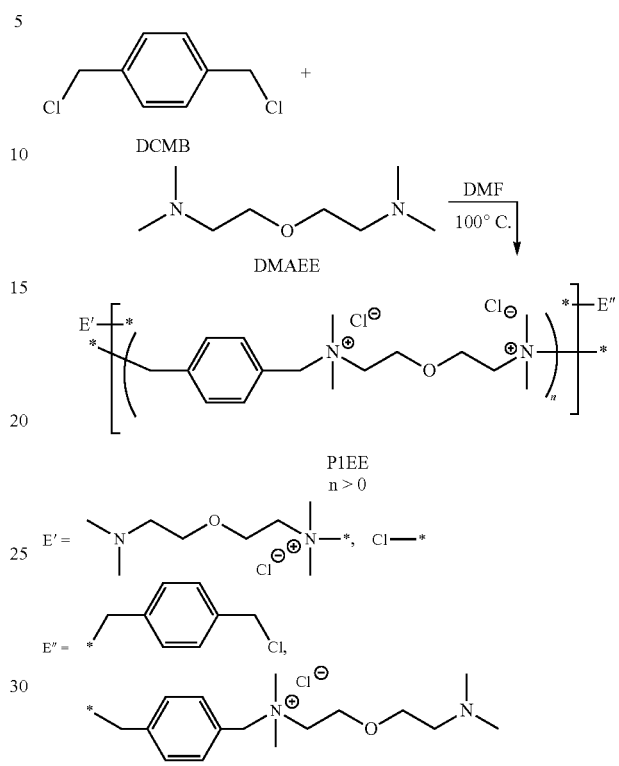

Figure 3:
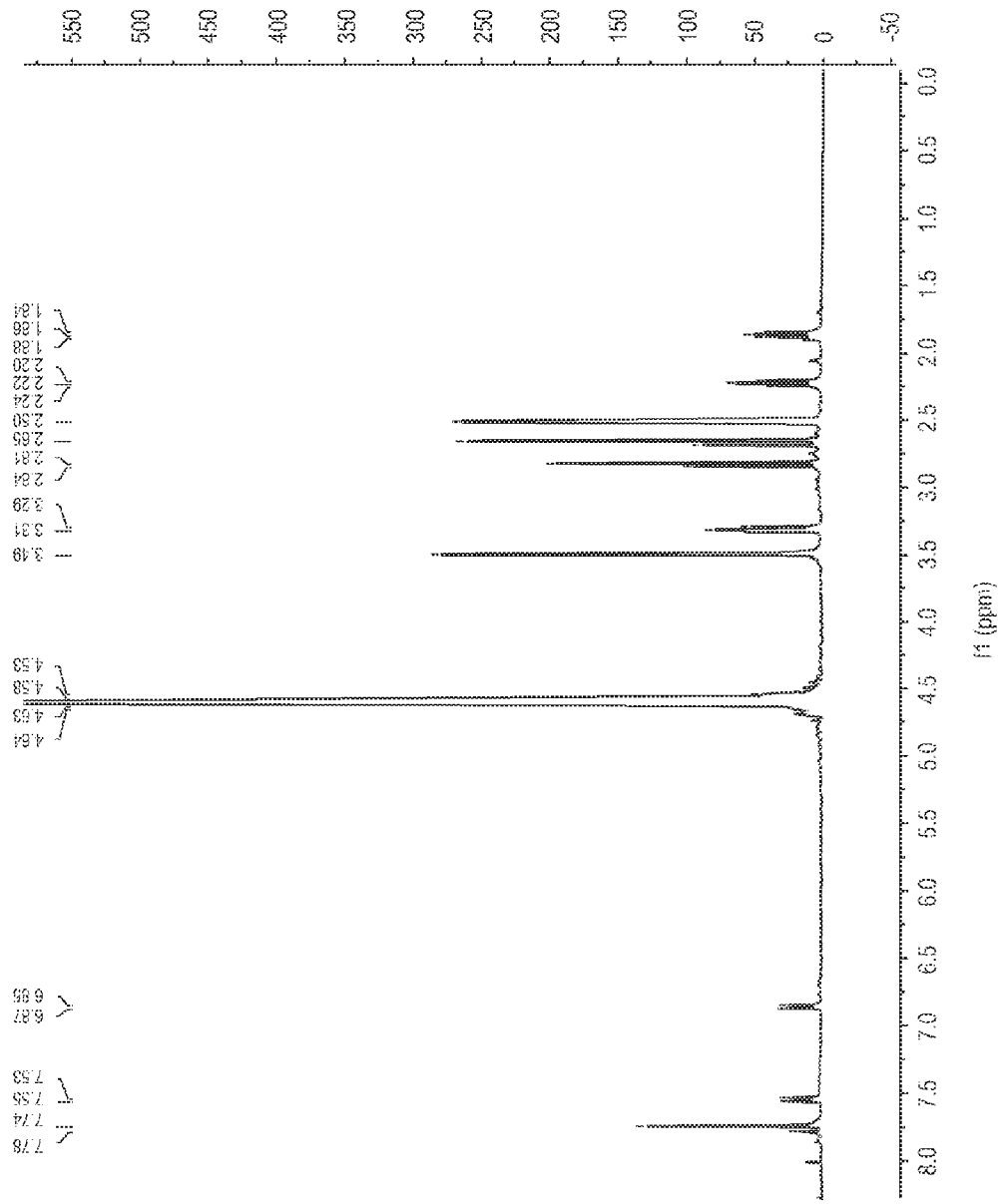
FIG. 3 is a $^1$H NMR spectrum of cationic polymer PIEE (Example 3).

Possible end groups E' and E" are listed above for a given macromolecule of cationic homopolymer P1EE (n>0). P1EE was prepared according to the general procedure of Example 1 using DCMB (1.65 g, 9.43 mmol) and DMAEE (1.51 g, 9.43 mmol, 1 eq.) and isolated in near quantitative yield. FIG. 3 is a $^1$H NMR spectrum of P1EE.

Example 4. Preparation of Cationic Homopolymer P1BP

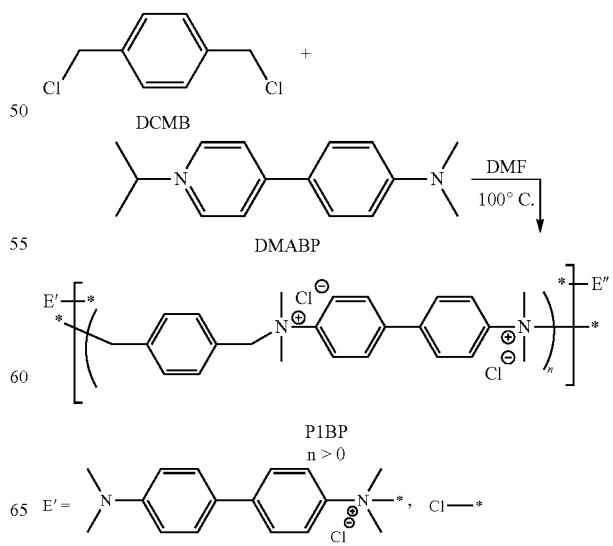

-continued

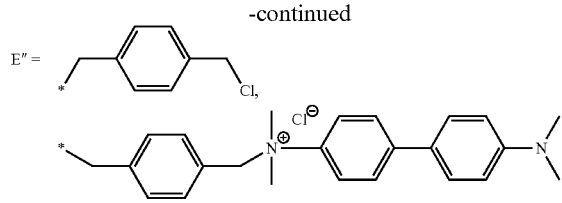

Figure 4:
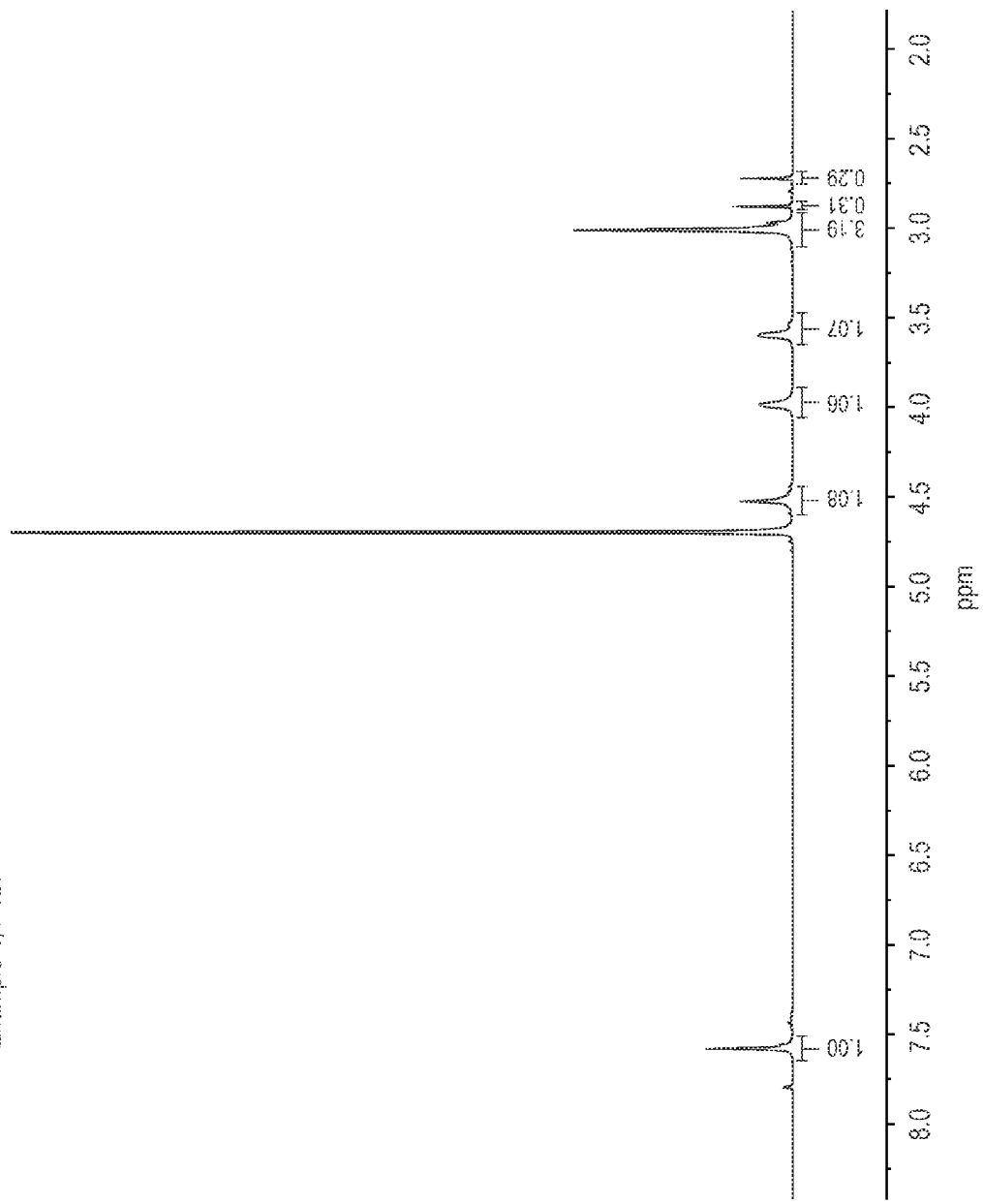
FIG. 4 is a $^1$H NMR spectrum of cationic polymer PIBP (Example 4).

Possible end groups E' and E" are listed above for a given macromolecule of cationic homopolymer P1BP (n>0). P1BP was prepared according to the general procedure of Example 1 using DCMB (0.928 g, 5.30 mmol) and DMABP (1.27 g, 5.30 mmol, 1 eq.) and isolated in near quantitative yield. FIG. 4 is a $^1$H NMR spectrum of P1BP.

Example 5. Preparation of Cationic Random Copolymer P2E8B

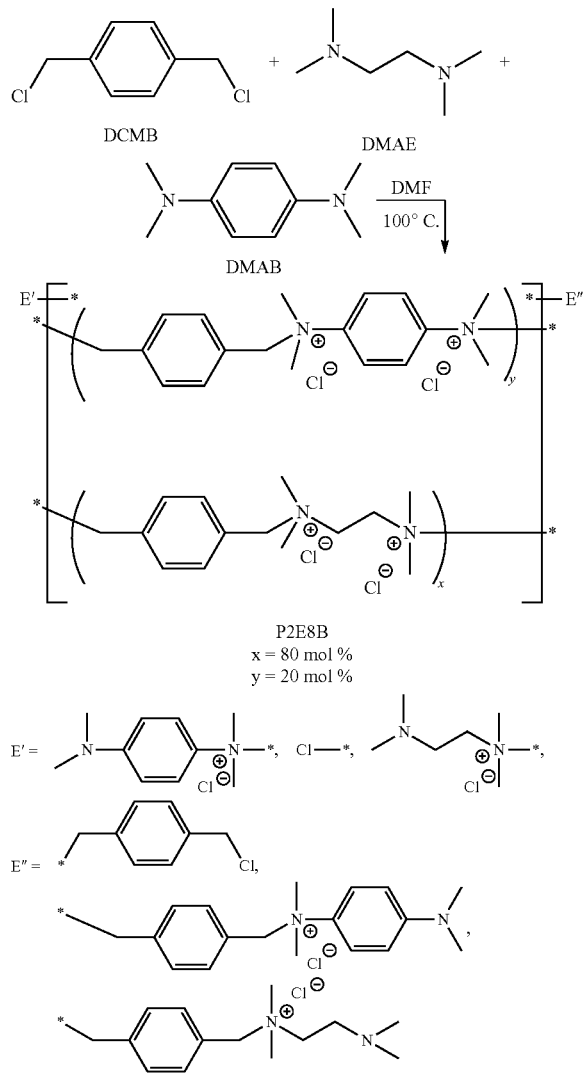

Figure 5:
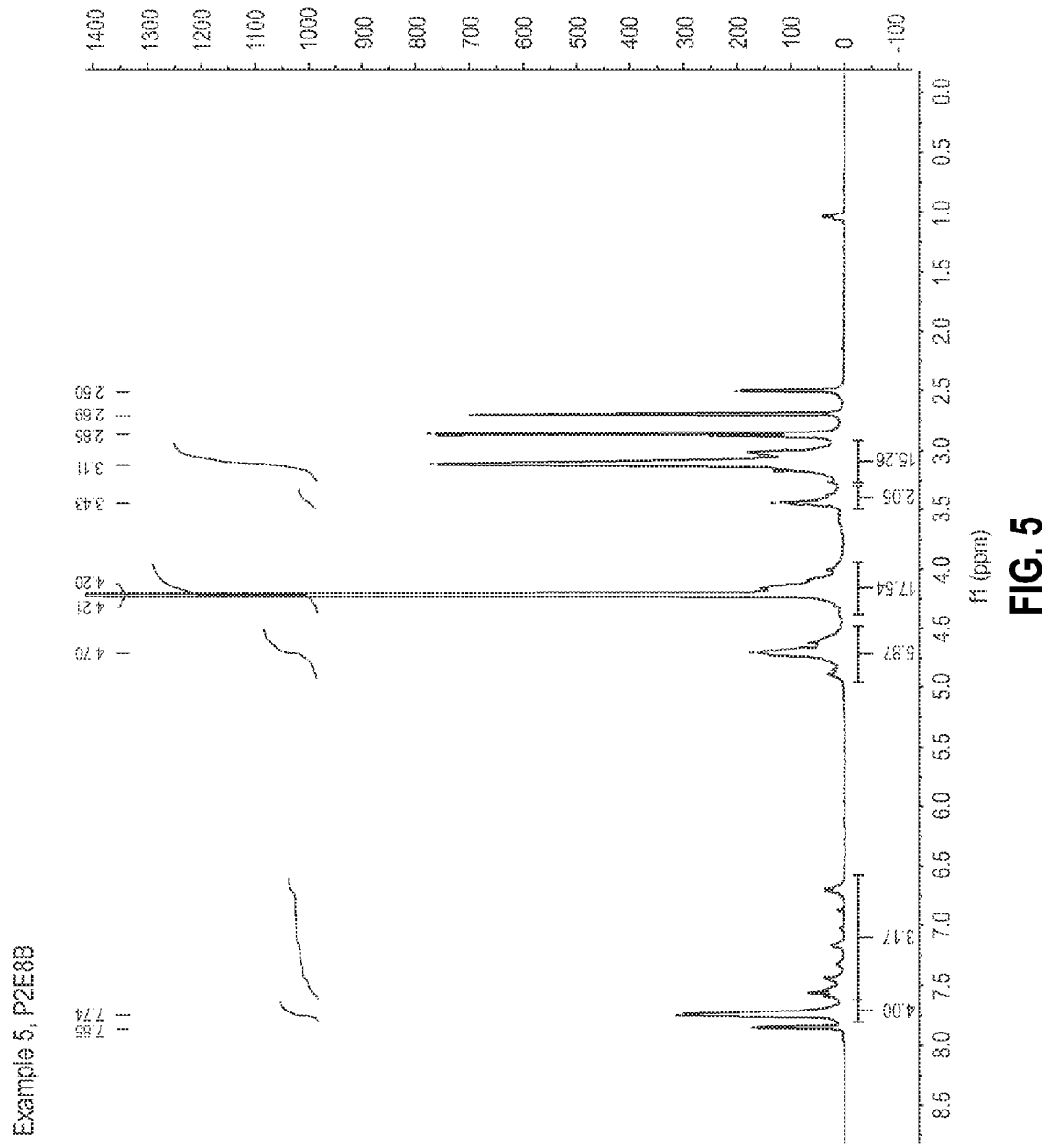
FIG. 5 is a $^1$H NMR spectrum of cationic polymer P2E8B (Example 5).

Possible end groups E' and E" are listed above for a given macromolecule of cationic random copolymer P2E8B (x:y=80:20 molar ratio). P2E8B (x:y=80:20 molar ratio) was prepared according to the general procedure of Example 1 using DCMB (1.75 g, 10.0 mmol), DMAE (0.930 g, 8.00 mmol, 0.8 eq.), and DMAB (0.329 g, 0.200 mmol, 0.2 eq.). Yield: 2.95 g, 98%. FIG. 5 is a $^1$H NMR spectrum of P2E8B.

Example 6

Figure 6:
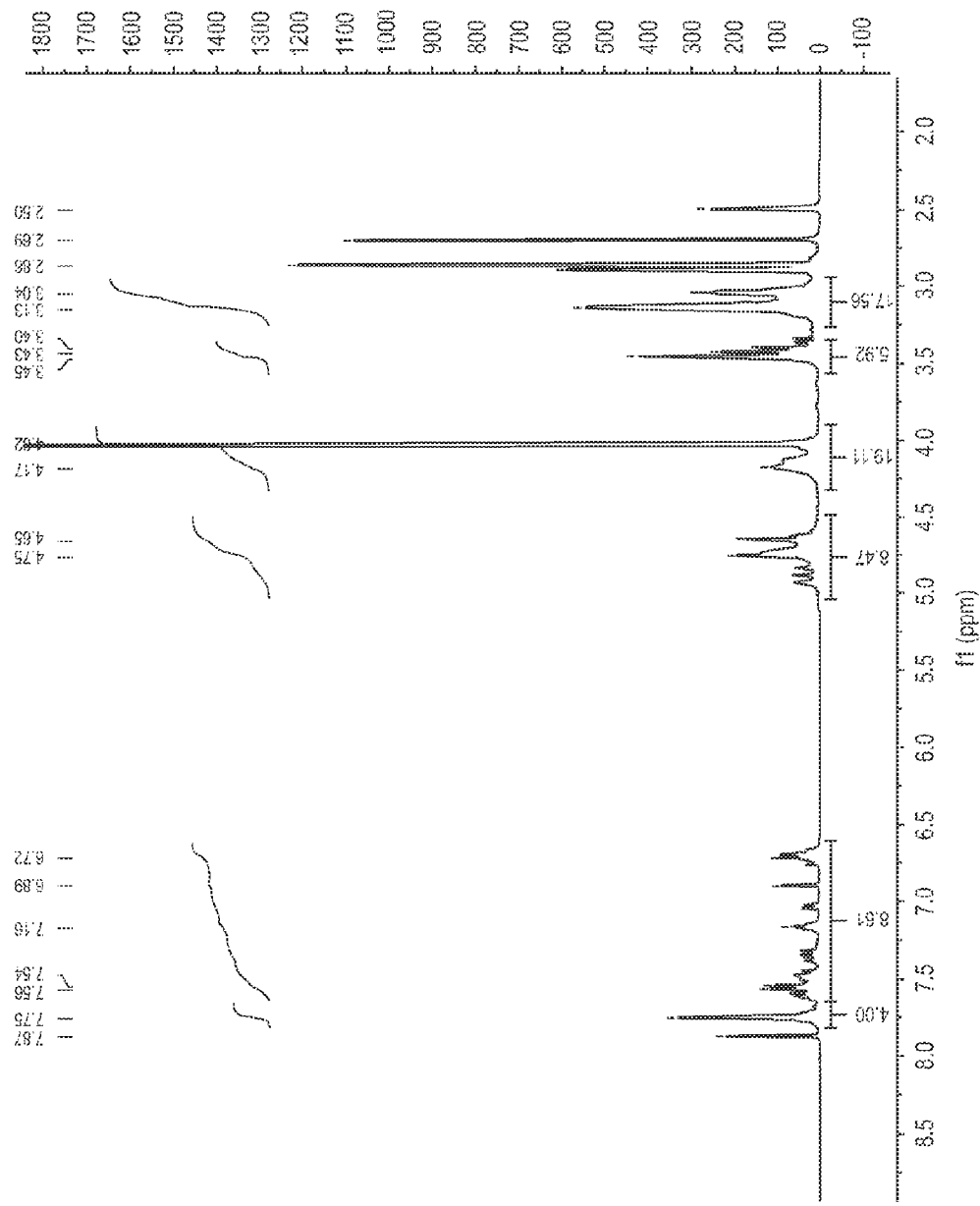
FIG. 6 is a $^1$H NMR spectrum of cationic polymer P2E6B (Example 6).

Preparation of cationic random copolymer P2E6B (x:y=60:40 molar ratio). P2E6B was prepared as Example 5 using a different x:y molar ratio. P2E6B was prepared using DCMB (1.75 g, 10.0 mmol), DMAE (0.697 g, 6.00 mmol, 0.6 eq.), and DMAB (0.657 g, 4.00 mmol, 0.4 eq.). Yield: 3.01 g, 97%. FIG. 6 is a $^1$H NMR spectrum of P2E6B.

Example 7

Figure 7:
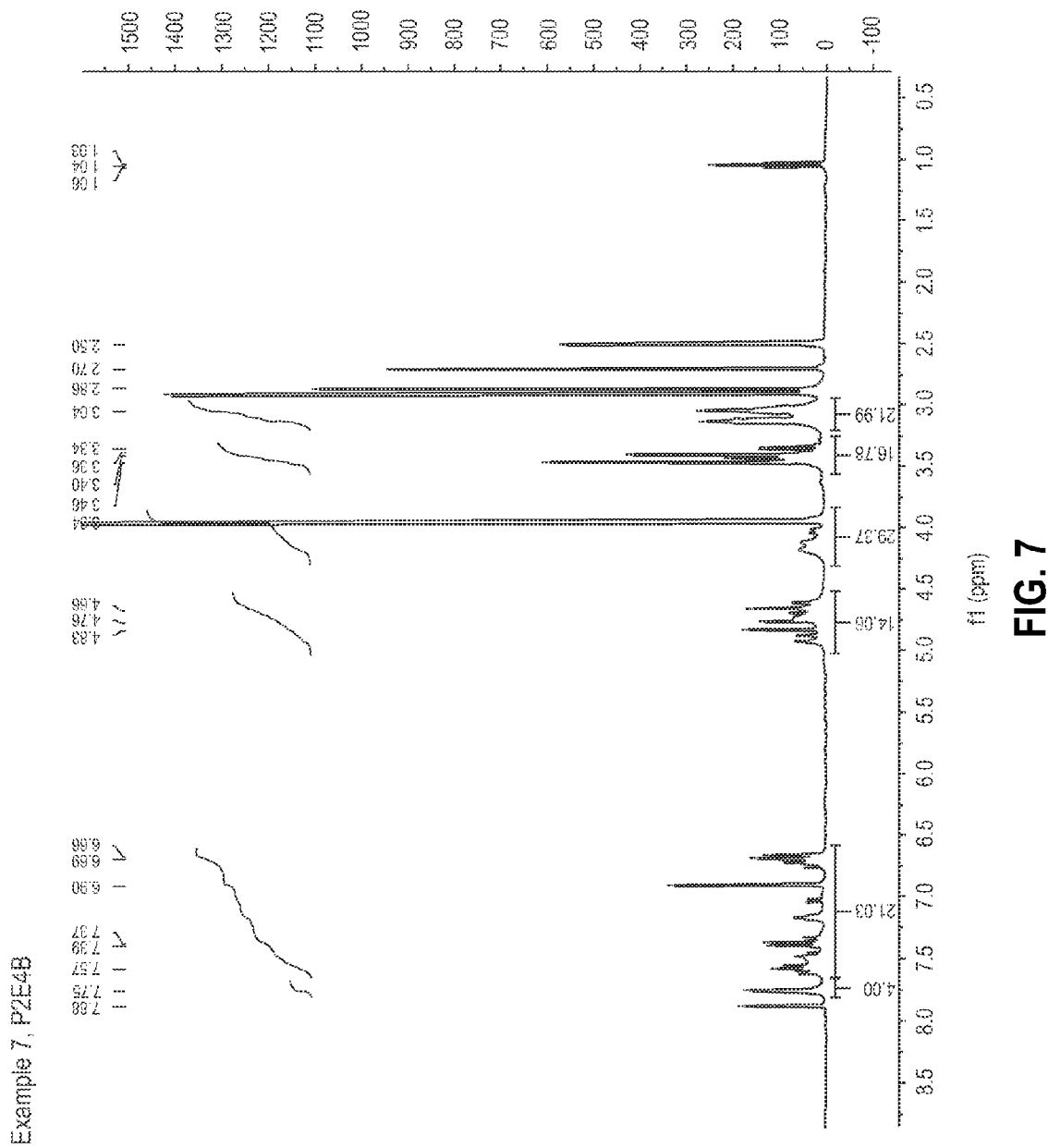
FIG. 7 is a $^1$H NMR spectrum of cationic polymer P2E4B (Example 7).

Preparation of cationic random copolymer P2E4B (x:y=40:60 molar ratio). P2E4B was prepared as Example 5 using a different x:y molar ratio. P2E4B prepared using DCMB (1.75 g, 10.0 mmol), DMAE (0.465 g, 4.00 mmol, 0.4 eq.), and DMAB (0.986 g, 6.00 mmol, 0.6 eq.). Yield: 2.94 g, 92%. FIG. 7 is a $^1$H NMR spectrum of P2E4B.

Example 8. Preparation of Cationic Random Copolymer P2E8BP

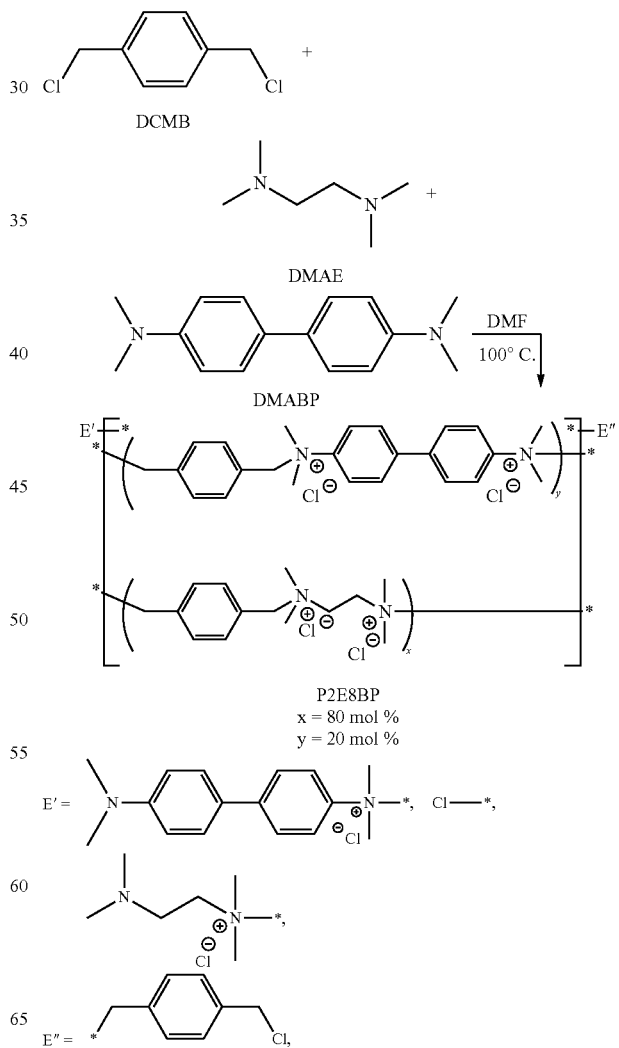

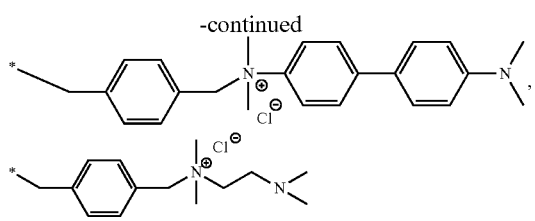

Figure 8:
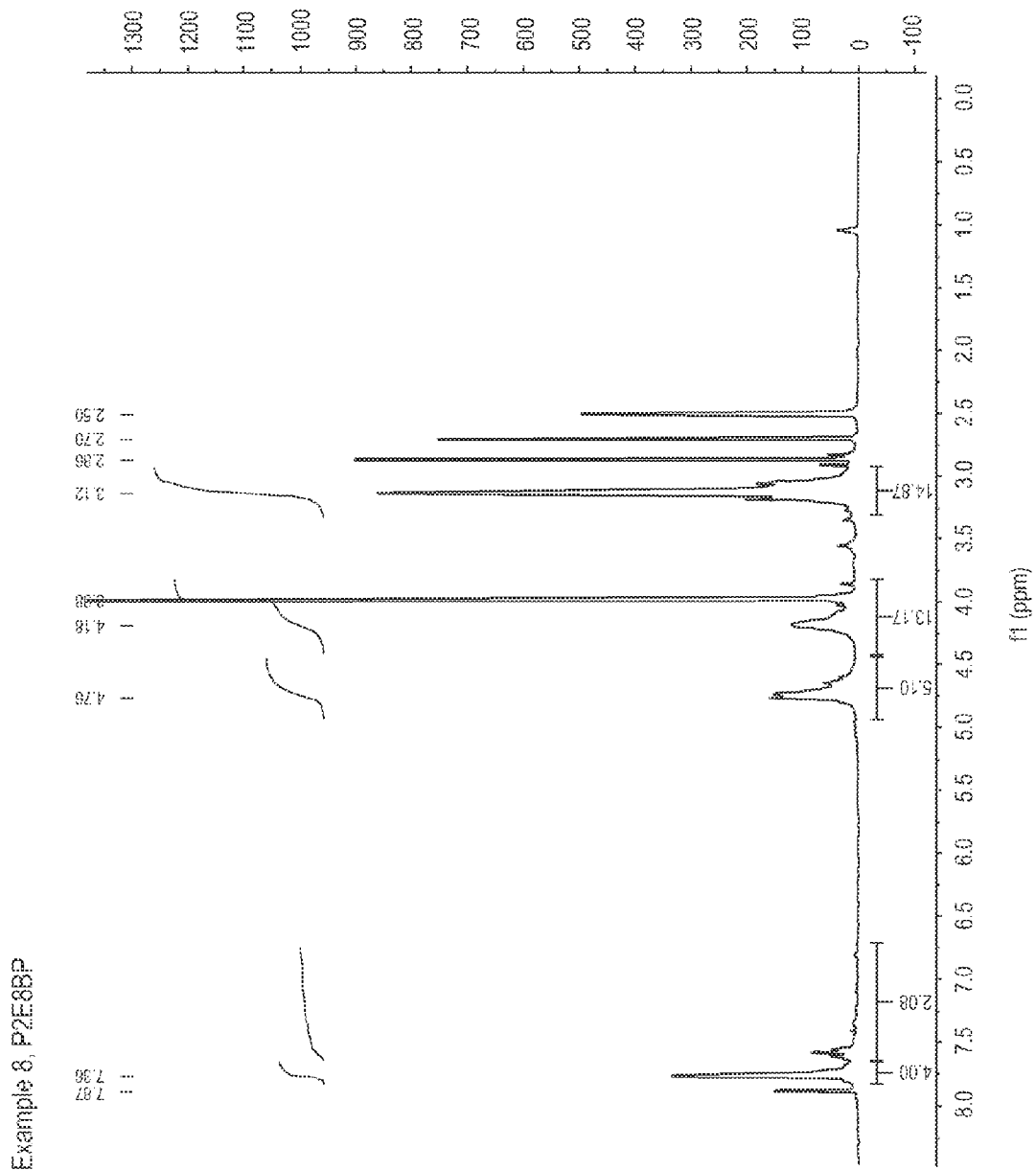
FIG. 8 is a $^1$H NMR spectrum of cationic polymer P2E8BP (Example 8).

Possible end groups E' and E" are listed above for a given macromolecule of cationic random copolymer P2E8BP (x:y=80:20 molar ratio) are listed above. P2E8BP was prepared according to the general procedure of Example 1 using DCMB (1.50 g, 8.57 mmol), DMAE (0.797 g, 6.86 mmol, 0.8 eq.), and DMAB (0.411 g, 1.71 mmol, 0.2 eq.). Yield: 2.31 g, 85%. FIG. 8 is a $^1$H NMR spectrum of P2E8B.

Example 9

Figure 9:
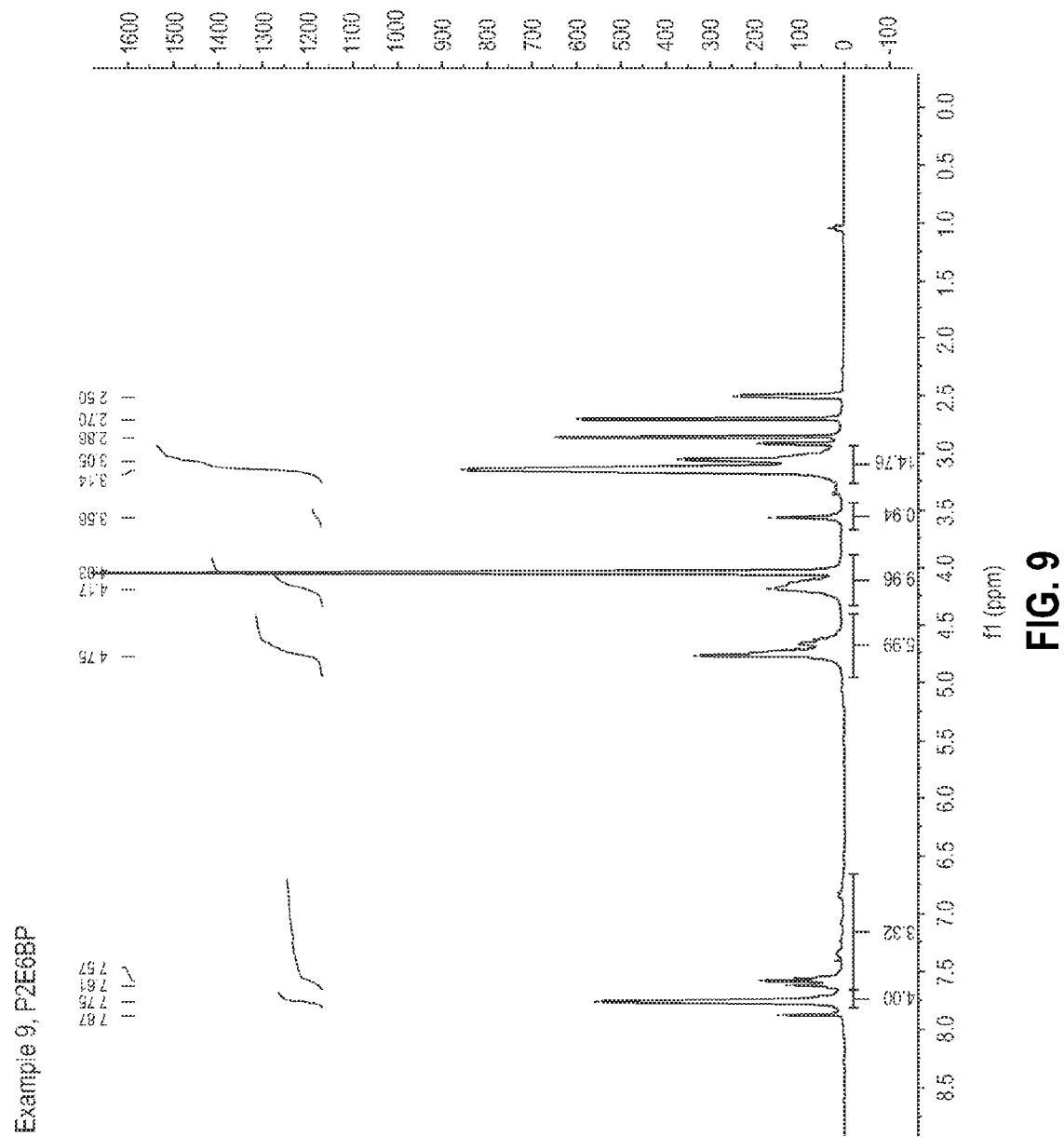
FIG. 9 is a $^1$H NMR spectrum of cationic polymer P2E6BP (Example 9).

Preparation of cationic random copolymer P2E6BP (x:y=60:40 molar ratio). P2E6BP was prepared as Example 9 using a different x:y molar ratio. P2E6BP was prepared using DCMB (1.50 g, 8.57 mmol), DMAE (0.597 g, 5.14 mmol, 0.6 eq.), and DMABP (0.824 g, 3.43 mmol, 0.4 eq.). Yield: 1.93 g, 66%. FIG. 9 is a $^1$H NMR spectrum of P2E6BP.

Example 10

Figure 10:
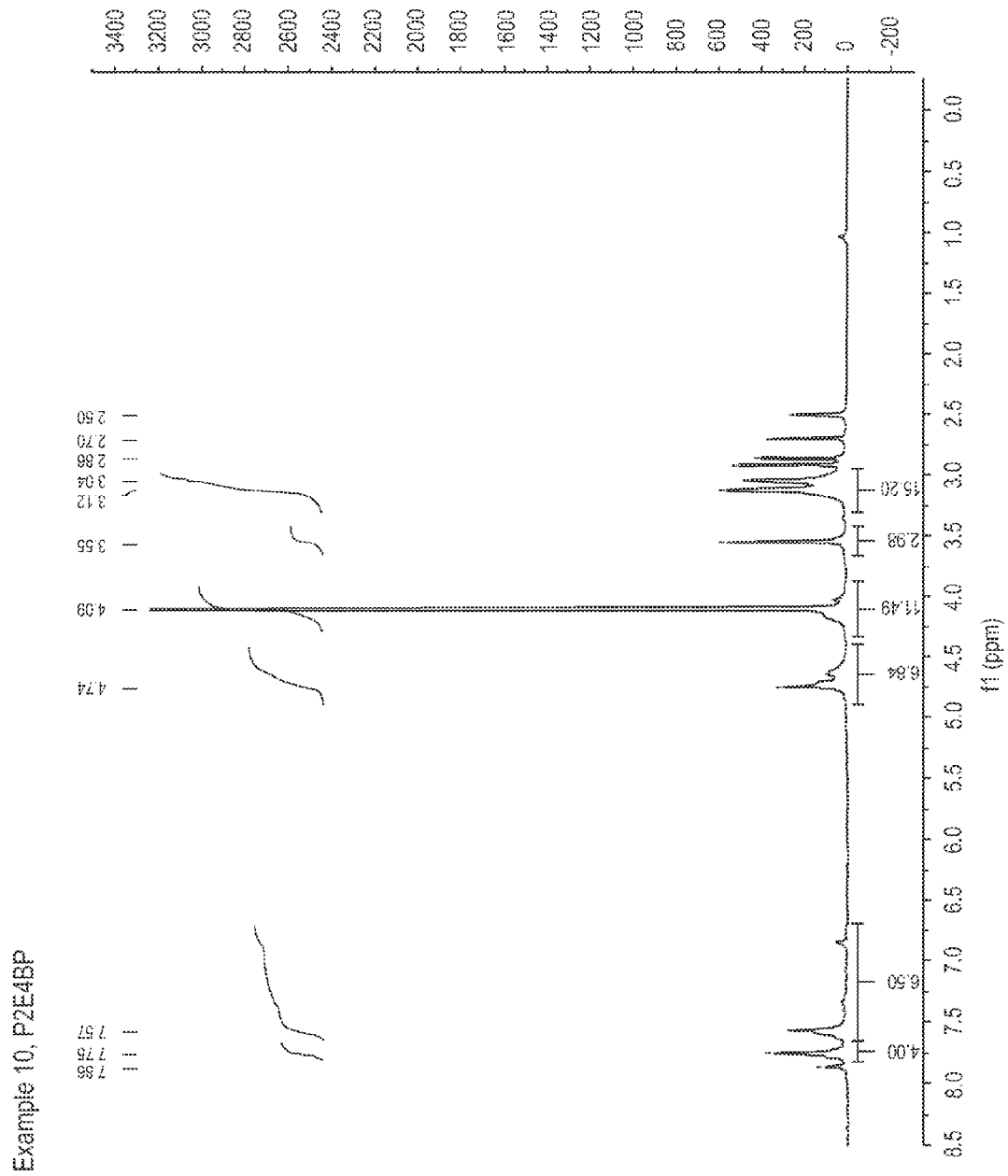
FIG. 10 is a $^1$H NMR spectrum of cationic polymer P2E4BP (Example 10).

Preparation of cationic random copolymer P2E4BP (x:y=40:60 molar ratio). P2E4PB was prepared as Example 9 using a different x:y molar ratio. P2E4BP was prepared using DCMB (1.50 g, 8.57 mmol), DMAE (0.399 g, 3.43 mmol, 0.4 eq.), and DMABP (1.24 g, 5.14 mmol, 0.6 eq.). Yield: 1.63 g, 52%. FIG. 10 is a $^1$H NMR spectrum of P2E4BP.

Example 11. Preparation of Cationic Random Copolymer P2EE8BP

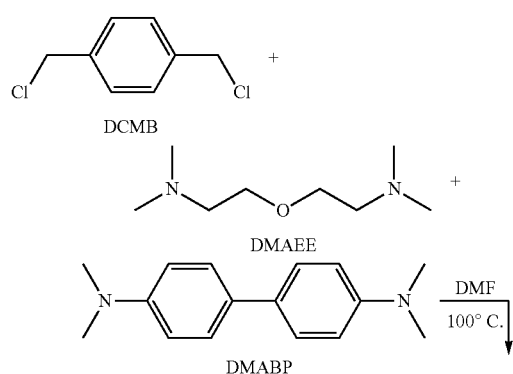

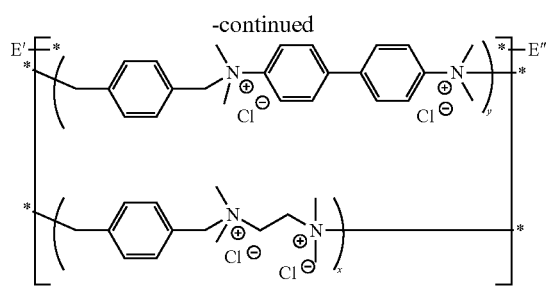

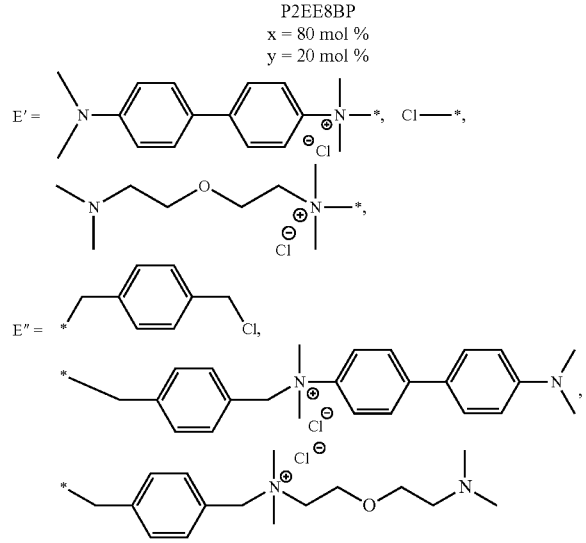

Figure 11:
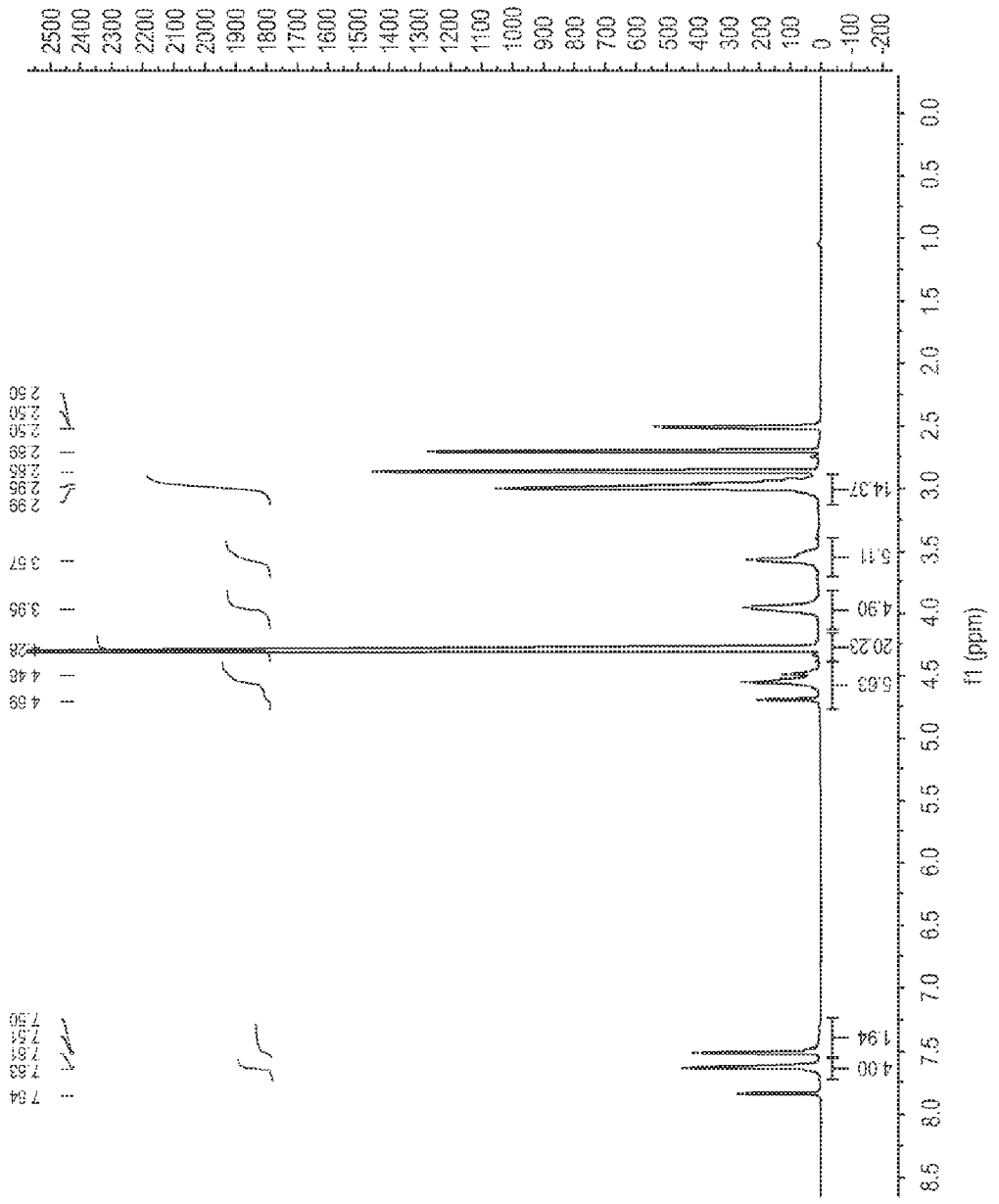
FIG. 11 is a $^1$H NMR spectrum of cationic polymer P2EE8BP (Example 11).

Possible end groups E' and E" are listed above for a given macromolecule of cationic random copolymer P2EE8BP (x:y=80:20 molar ratio). P2EE8BP was prepared according to the general procedure of Example 1 using DCMB (1.50 g, 8.57 mmol), DMAEE (1.10 g, 6.86 mmol, 0.8 eq.), and DMAB (0.412 g, 1.71 mmol, 0.2 eq.). Yield: 2.84 g, 94%. FIG. 11 is a $^1$H NMR spectrum of P2EE8BP.

Example 12

Figure 12:
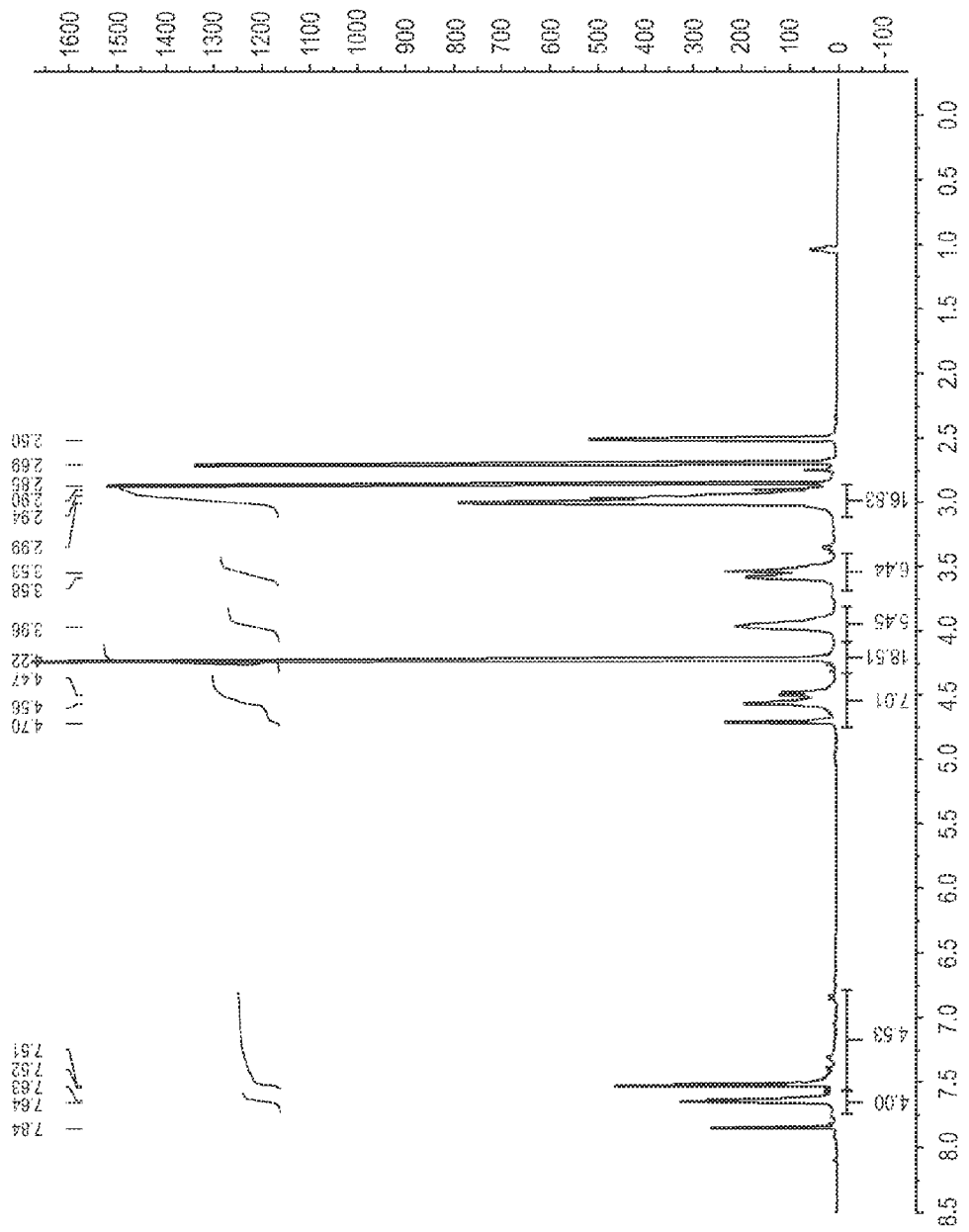
FIG. 12 is a $^1$H NMR spectrum of cationic polymer P2EE6BP (Example 12).

Preparation of cationic random copolymer P2EE6BP (x:y=60:40 molar ratio). P2EE6BP was prepared as Example 12 using a different x:y molar ratio. P2EE6BP was prepared using DCMB (1.50 g, 8.57 mmol), DMAE (0.824 g, 5.14 mmol, 0.6 eq.), and DMABP (0.824 g, 3.43 mmol, 0.4 eq.). Yield: 1.99 g, 63%. FIG. 12 is a $^1$H NMR spectrum of P2EE6BP

Example 13

Figure 13:
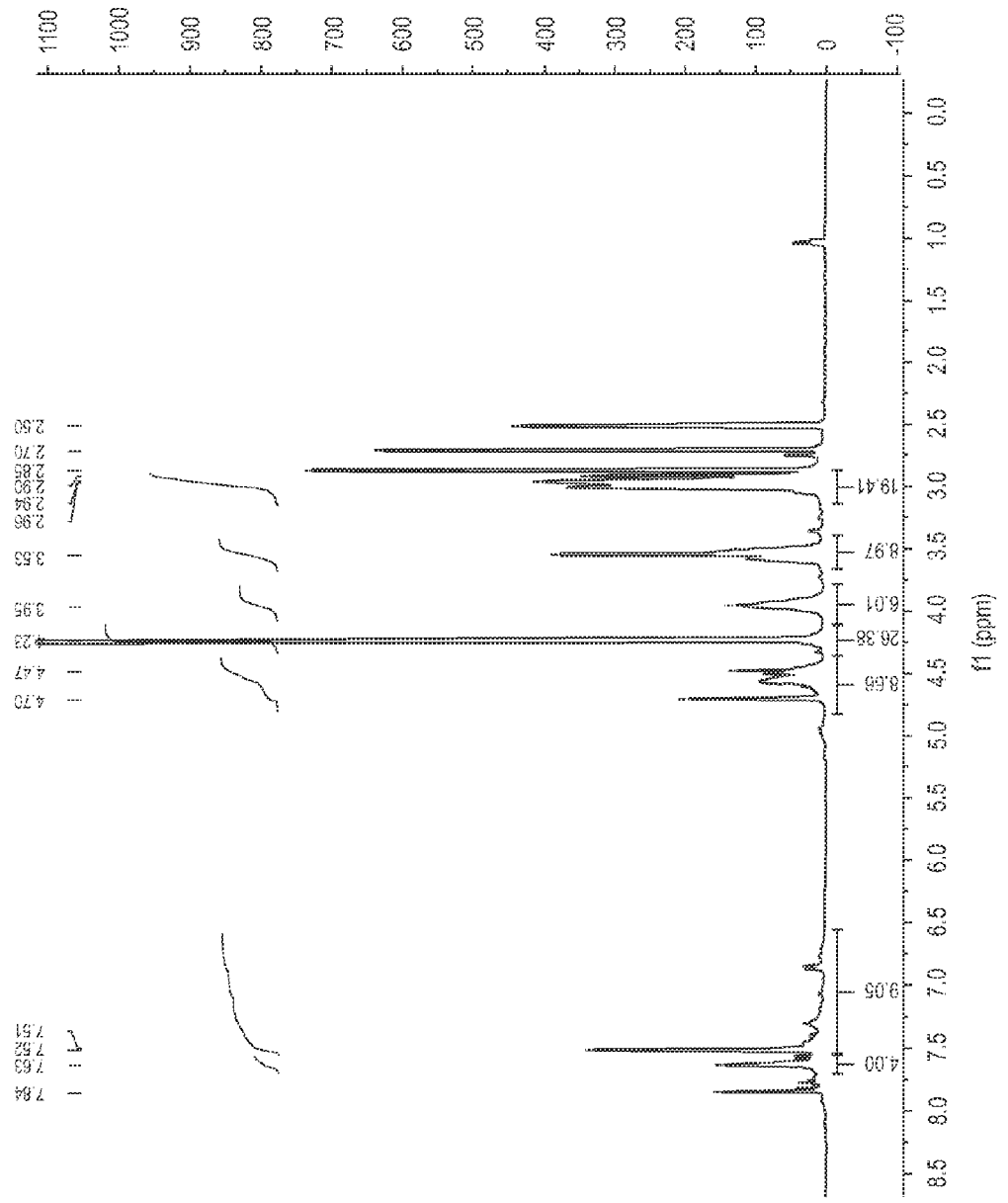
FIG. 13 is a $^1$H NMR spectrum of cationic polymer P2EE4BP (Example 13).

Preparation of cationic random copolymer P2EE4BP (x:y=40:60 molar ratio). P2EE4PB was prepared as Example 12 using a different x:y molar ratio. P2EE4BP was prepared using DCMB (1.50 g, 8.57 mmol), DMAE (0.550 g, 3.43 mmol, 0.4 eq.), and DMABP (1.24 g, 5.14 mmol, 0.6 eq.). Yield: 1.91 g, 58%. FIG. 13 is a $^1$H NMR spectrum of P2EE4BP.

Table 2 summarizes the cationic polymers formed.

TABLE 2

| Example | Polymer Name | Dihalide | Dihalide (g, mmol) | Diamine 1 | Diamine 1 (g, mmol, eq.) | Diamine 2 | Diamine 2 (g, mmol, eq.) | Solvent | Temp (° C.) | Time (hours) | Yield (%) |
|---|---|---|---|---|---|---|---|---|---|---|---|
| 1 | P1E | DCMB | 1.01, 5.76 | DMAE | 0.669, 5.76, 1.0 | | | DMF | 100 | 18 | >99 |
| 2 | P1B | DCMB | 0.974, 5.50 | DMAB | 0.915, 5.50, 1.0 | | | DMF | 100 | 18 | >99 |
| 3 | P1EE | DCMB | 1.65, 9.43 | DMAEE | 1.51, 9.43, 1.0 | | | DMF | 100 | 18 | >99 |

TABLE 2-continued

| Example | Polymer Name | Dihalide | Dihalide (g, mmol) | Diamine 1 | Diamine 1 (g, mmol, eq.) | Diamine 2 | Diamine 2 (g, mmol, eq.) | Solvent | Temp (° C.) | Time (hours) | Yield (%) |
|---|---|---|---|---|---|---|---|---|---|---|---|
| 4 | P1BP | DCMB | 0.928, 5.30 | DMABP | 1.27, 5.30, 1.0 | | | DMF | 100 | 18 | >99 |
| 5 | P2E8B | DCMB | 1.75, 10.0 | DMAE | 0.930, 8.00, 0.8 | DMAB | 0.329, 2.00, 0.2 | DMF | 100 | 18 | 98 |
| 6 | P2E6B | DCMB | 1.75, 10.0 | DMAE | 0.697, 6.00, 0.6 | DMAB | 0.657, 4.00, 0.4 | DMF | 100 | 18 | 97 |
| 7 | P2E4B | DCMB | 1.75, 10.0 | DMAE | 0.465, 4.00, 0.4 | DMAB | 0.986, 6.00, 0.6 | DMF | 100 | 18 | 92 |
| 8 | P2E8BP | DCMB | 1.50, 8.57 | DMAE | 0.797, 6.86, 0.8 | DMABP | 0.411, 1.71, 0.2 | DMF | 100 | 18 | 85 |
| 9 | P2E6BP | DCMB | 1.50, 8.57 | DMAE | 0.597, 5.14, 0.6 | DMABP | 0.824, 3.43, 0.4 | DMF | 100 | 18 | 66 |
| 10 | P2E4BP | DCMB | 1.50, 8.57 | DMAE | 0.399, 3.43, 0.4 | DMABP | 1.24, 5.14, 0.6 | DMF | 100 | 18 | 52 |
| 11 | P2EE8BP | DCMB | 1.50, 8.57 | DMAEE | 1.10, 6.86, 0.8 | DMABP | 0.412, 1.71, 0.2 | DMF | 100 | 18 | 94 |
| 12 | P2EE6BP | DCMB | 1.50, 8.57 | DMAEE | 0.824, 5.14, 0.6 | DMABP | 0.824, 3.43, 0.4 | DMF | 100 | 18 | 63 |
| 13 | P2EE4BP | DCMB | 1.50, 8.57 | DMAEE | 0.550, 3.43, 0.4 | DMABP | 1.24, 5.14, 0.6 | DMF | 100 | 18 | 58 |

Table 3 summarizes the molecular weight properties of the cationic polymers formed.

TABLE 3

| Example | Polymer Name | Dihalide | Diamine 1 | Diamine 2 | Mw | Mn | PDI |
|---|---|---|---|---|---|---|---|
| 1 | P1E | DCMB | DMAE | | 6767 | 3506 | 1.93 |
| 2 | P1B | DCMB | DMAB | | | | |
| 3 | P1EE | DCMB | DMAEE | | 20600 | 7930 | 2.60 |
| 4 | P1BP | DCMB | DMABP | | | | |
| 5 | P2E8B | DCMB | DMAE | DMAB | 7617 | 3559 | 2.14 |
| 6 | P2E6B | DCMB | DMAE | DMAB | 5100 | 2860 | 1.78 |
| 7 | P2E4B | DCMB | DMAE | DMAB | 5500 | 3680 | 1.49 |
| 8 | P2E8BP | DCMB | DMAE | DMABP | | | |
| 9 | P2E6BP | DCMB | DMAE | DMABP | | | |
| 10 | P2E4BP | DCMB | DMAE | DMABP | | | |
| 11 | P2EE8BP | DCMB | DMAEE | DMABP | 5497 | 2656 | 2.07 |
| 12 | P2EE6BP | DCMB | DMAEE | DMABP | 4690 | 2080 | 2.25 |
| 13 | P2EE4BP | DCMB | DMAEE | DMABP | | | |

The polymer P1E is water soluble, and has a Mw of 6767 and polydispersity index of 1.93. Polymers P1B and P1BP have more rigid structure and higher hydrophobicity as compared to P1E. Therefore, P1B and P1BP have limited water solubility.

Minimum Inhibitory Concentration (MIC)

Antimicrobial activity of P1E was assessed against four different microbes of clinical relevance, *Staphylococcus aureus* (*S. aureus*), *Escherichia coli* (*E. coli*), *Pseudomonas aeruginosa* (*P. aeruginosa*), and *Candida albicans* (*C. albicans*). The minimum inhibitory concentrations (MICs) against all microbes were determined using the broth microdilution method, and were taken to be the lowest concentration where no observable microbial growth was detected by the microplate reader after the incubation duration with an initial microbial loading of $3 \times 10^5$ CFU/mL.

Bacterial and fungal samples were inoculated in Mueller-Hinton broth (MHB) at 37° C. and room temperature, respectively, under constant shaking of 100 rpm. The samples were grown overnight to enter the log growth phase. A broth microdilution method was used to determine the respective MIC of each polymer, where 100 microliters of broth containing a polymer with a constant de-ionized (DI) water content of 20% volume/volume at various concentrations was placed in each well of a 96-well culture plate. Prior to the addition of an equal volume of microbial solution into each well, the concentration of the microbial solution was first adjusted to obtain an optical density (O.D.) reading of approximately 0.07 at 600 nm using a microplate reader (TECAN, Switzerland), which corresponds to the concentration of McFarland 1 solution of $3 \times 10^8$ CFU/mL and followed by a 1000-time dilution to achieve an initial loading of $3 \times 10^5$ CFU/mL. The 96-well plate was then incubated at 37° C. for bacterial samples and room temperature for fungi samples under constant shaking of 100 rpm for 18 hours and 42 hours, respectively. MIC was regarded to be the least concentration where no observable microbial growth was detected by the microplate reader after the incubation duration. Broth containing only microbes was used as the negative control. Six replicates were tested for each concentration of polymer and the control.

Hemolysis Assay

Toxicity of polymers was evaluated via the hemolysis assay with fresh rat red blood cells (RBCs). An RBC suspension was diluted 25 times with phosphate buffered saline (PBS) to achieve 4% v/v blood content. Polymers were dissolved in PBS at various concentrations with a constant deionized water (DI) water concentration of 20% volume/volume. Diluted blood suspension was treated with an equal volume of polymer solution and incubated at 37° C. for 1 hour. After centrifugation of the mixtures at 1000 g-force for 5 minutes at 4° C., 100 microliters of supernatant was transferred into a 96-well culture plate, with 4 replicates for each polymer concentration. The hemoglobin released was then measured using a microplate reader (TECAN, Switzerland) at 576 nm. Untreated RBCs suspension was used as the negative control while RBCs suspension treated with 0.1% Triton-X was the positive control. Percentage of hemolysis was calculated as follows:

Hemolysis (%)=[(O.D.$_{576\ nm}$ of the treated sample−O.D.$_{576\ nm}$ of negative control)/(O.D.$_{576\ nm}$ of positive control−O.D.$_{576\ nm}$ of negative control)]×100%

Table 4 lists the MIC and 50% hemolysis (HC$_{50}$) values of various polymers. More than one value for a given microbe indicates a duplicate test.

TABLE 4

| Example | Polymer Name | MIC (mg/L) | | | | HC$_{50}$ (mg/L) |
|---|---|---|---|---|---|---|
| | | S. aureus | E. coli | P. aeruginosa | C. albicans | |
| 1 | P1E | 3.9 | 7.8 | 3.9, 7.8 | 7.8, 15.6 | >1000 |
| 2 | P1B | 7.8 | 31.3 | 250 | 31.3 | ≈187.5 (purified) |
| 3 | P1EE | 3.9 | 3.9 | 3.9 | 3.9 | >1000 |
| 4 | P1BP | | | Insoluble in water and organic solvents | | |
| 5 | P2E8B | 1.95 | 3.9 | 3.9 | 3.9 | 1000 |
| 6 | P2E6B | 1.95 | 3.9 | 3.9 | 3.9 | ~500 |
| 7 | P2E4B | 1.95 | 3.9 | 3.9 | 3.9 | ~500 |
| 8 | P2E8BP | | | Insoluble in water and organic solvents | | |
| 9 | P2E6BP | | | Insoluble in water and organic solvents | | |
| 10 | P2E4BP | | | Insoluble in water and organic solvents | | |
| 11 | P2EE8BP | 1.95 | 3.9 | 1.95 | 7.8 | >1000 |
| 12 | P2EE6BP | 1.95 | 3.9 | 3.9 | 7.8 | >1000 |
| 13 | P2EE4BP | | | Insoluble in water and organic solvents | | |

Polymer P1B shows lower antimicrobial activity than P1E as it precipitates out from the bacterial culture medium. Polymers P1EE and P1DH were synthesized in order to reduce cytotoxicity.

Figure 14:
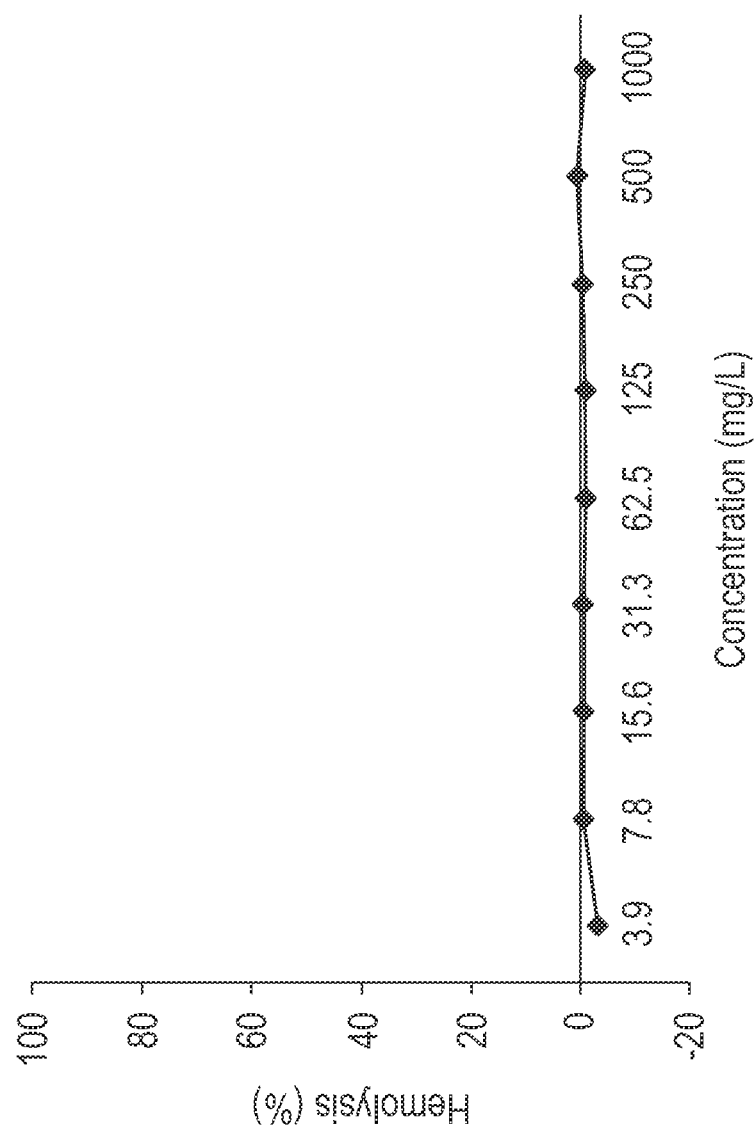
FIG. 14 is a graph showing the percent hemolysis as a function of concentration of cationic polymer PIE.

Polymers P1E, P1EE, P2E8B, P2E6B, P2E4B, P2EE8BP, and P2EE6BP were the most potent against both Gram-positive and Gram-negative bacteria as well as fungi with MICs of 3.9-15.6 mg/L. The polymers did not induce any significant hemolysis up to a concentration of 1000 mg/L. As an example, FIG. 14 is a graph showing the hemolytic behavior of cationic polymer PE at different concentrations, where negligible hemolysis was observed up to 1000 mg/L. Polymer P1DH did not exhibit activity up to 1000 mg/L against most of the microbes tested, possibly due to the presence of a number of hydroxyl groups, while P1EE is effective against all the microbes at a very low concentration (3.9 mg/L).

Killing Efficiency

The same procedure as described for MIC measurement was used to determine the concentration of polymer which kills the microbes, and the microbial samples were inoculated and prepared accordingly. After a given incubation (bacterial samples for 18 hours, and fungi samples for 42 hours), wells containing polymers at various concentrations of 0.0 MIC (0 times MIC), 0.5 MIC, 1.0 MIC, and 2.0 MIC were collected individually and diluted through a series of tenfold dilutions. The diluted microbial solution (20 microliters) was streaked onto an agar plate (LB Agar from 1st Base). The plates were then incubated for 18 hours at 37° C. for bacterial samples, or for 42 hours at room temperature for fungi samples. The colony-forming units on each plate were then counted.

Killing Kinetics

The same procedure as described for the killing efficiency test was used to assess the duration required for polymers to achieve 99.9% killing efficiency of microbes. Six time points of 0 minutes, 2 minutes, 10 minutes, 20 minutes, 1 hour and 2 hours were selected, and the microbes were treated at several-fold higher than the MIC concentrations.

Figure 15:
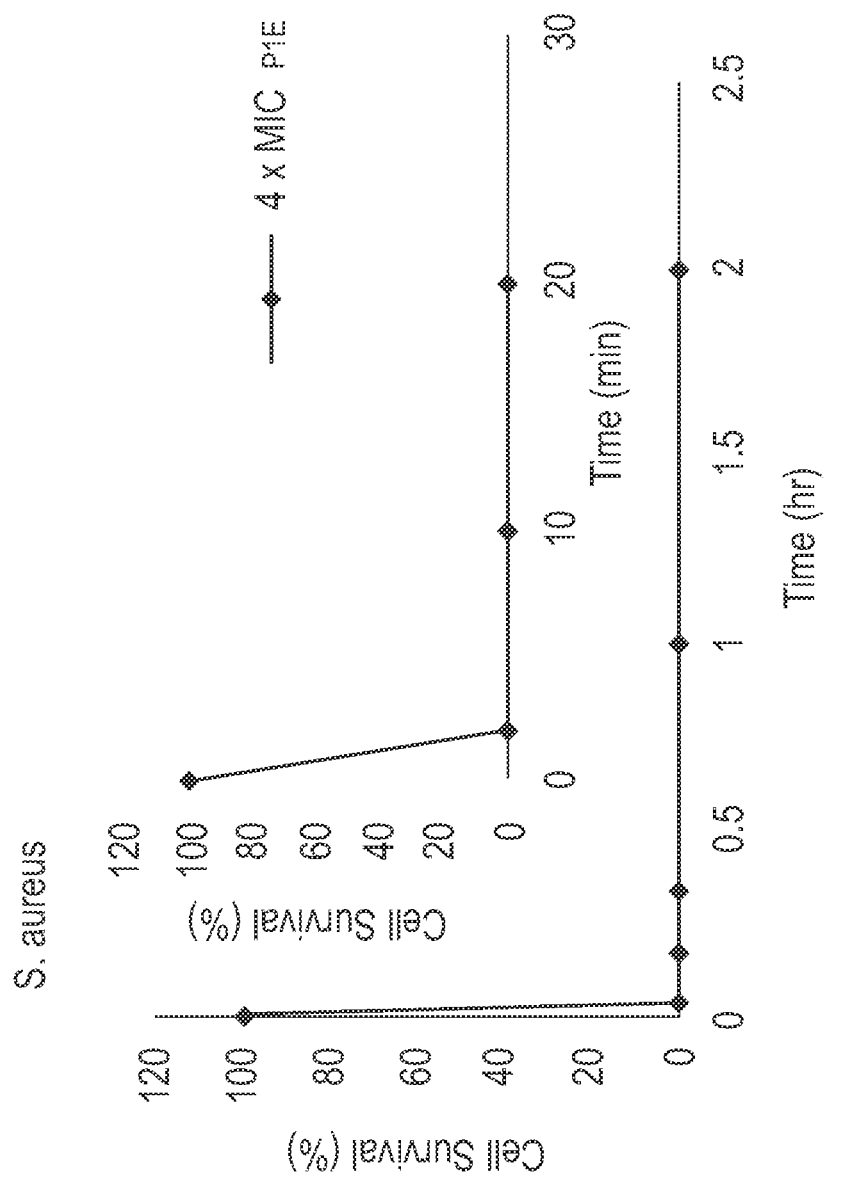
FIG. 15 is a graph showing the killing kinetics of cationic polymer PIE at 15.6 mg/L (4.0 MIC) against *Staphylococcus aureus* (*S. aureus*), where the initial bacterial loading was $3\times10^5$ CFU/mL.
Figure 16:
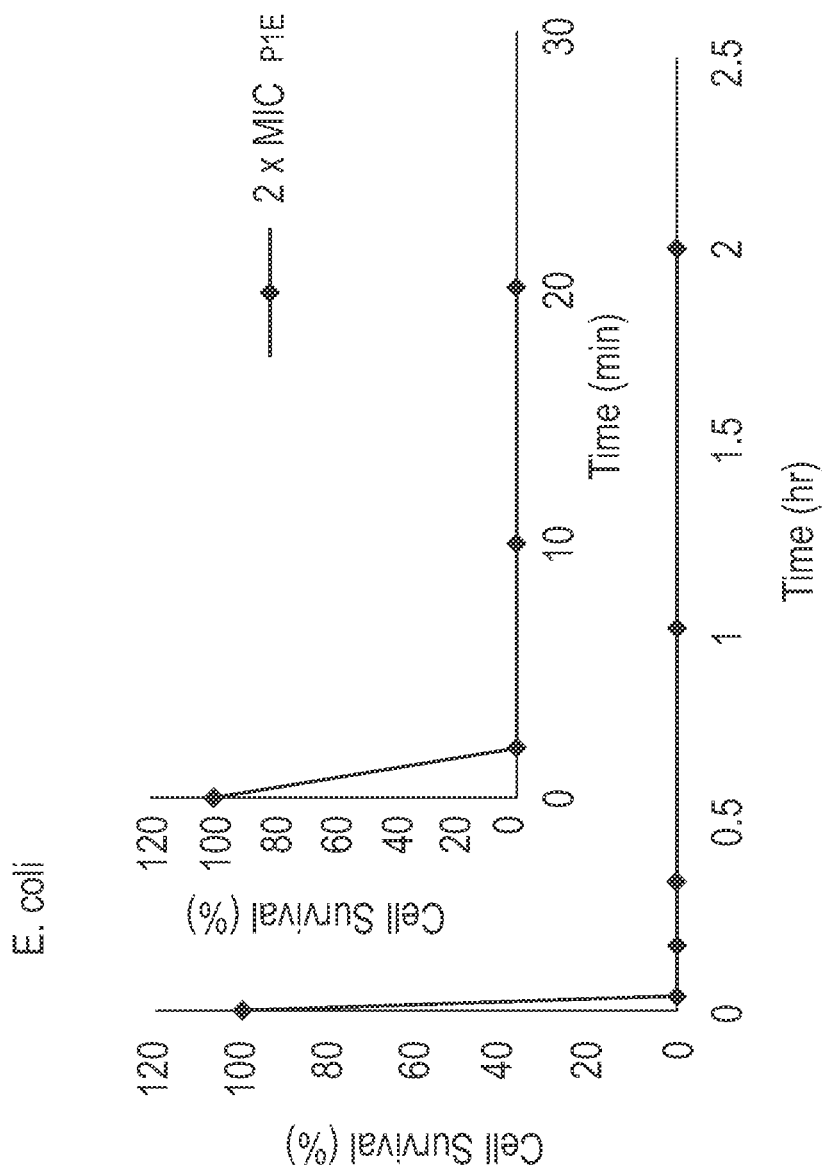
FIG. 16 is a graph showing the killing kinetics of cationic polymer PIE at 15.6 mg/L (2.0 MIC) against *Escherichia coli* (*E. coli*), where the initial bacterial loading was $3\times10^5$ CFU/mL.
Figure 17:
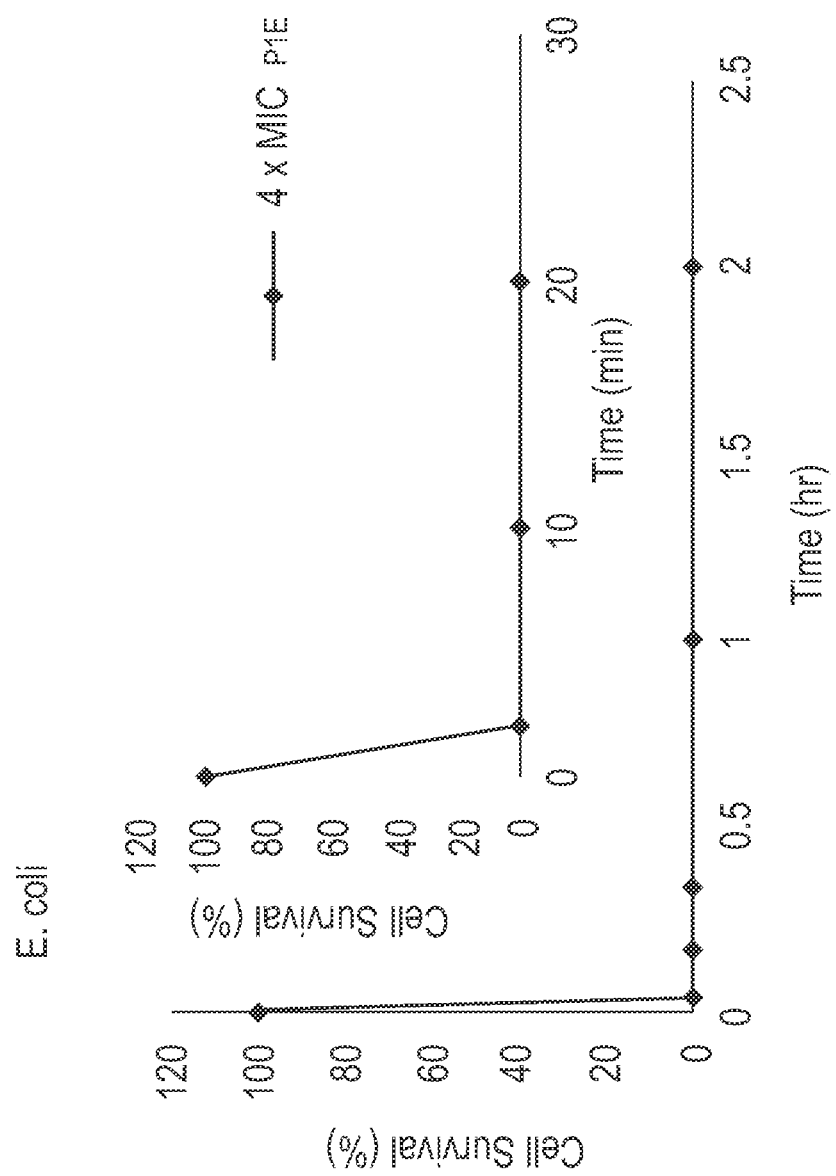
FIG. 17 is a graph showing the killing kinetics of cationic polymer PIE at 31.3 mg/L (4.0 MIC) against *Escherichia coli* (*E. coli*), where the initial bacterial loading was $3\times10^5$ CFU/mL.
Figure 18:
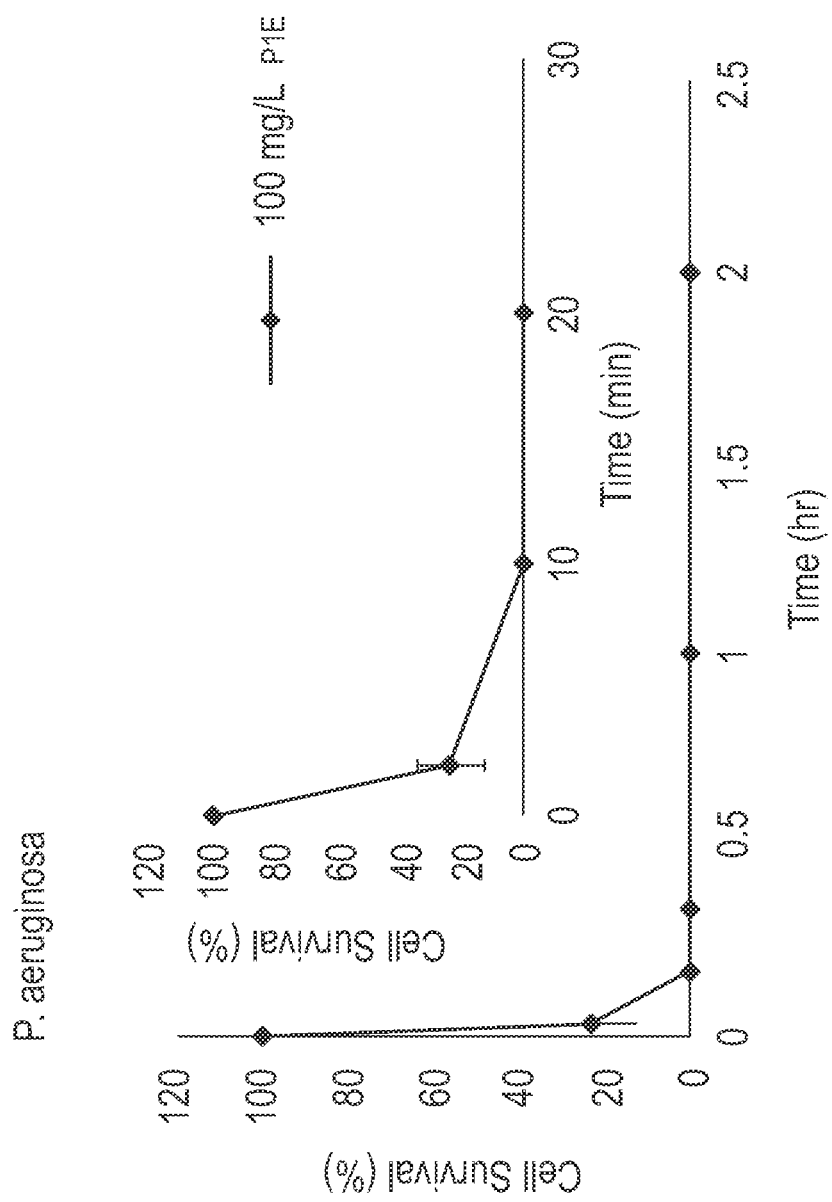
FIG. 18 is a graph showing the killing kinetics of cationic polymer PIE at 100.0 mg/L (4.0 MIC) against *P. aeruginosa*, where the initial bacterial loading was $3\times10^5$ CFU/mL.

The respective killing kinetics of P1E on Gram-positive S. aureus and Gram-negative E. coli was evaluated. As illustrated in FIG. 15, HT killed S. aureus with more than 99% efficiency within 2 minutes, and eradicated all the bacterial cells in 10 minutes at 4.0 MIC (i.e., 15.6 mg/L). In the case of E. coli, the killing efficiency of PIE was almost 100% at concentrations of 15.6 mg/L (FIG. 16) and 31.3 mg/L (FIG. 17) after 2 minutes. For P. aeruginosa, the killing efficiency was 99.5% and ~100% at 10 minutes and 20 minutes, respectively, using a concentration of 100 mg/L (FIG. 18).

In Vitro Cytotoxicity

Cytotoxicity of polymers was investigated by MTT assay, where human dermal fibroblast cells (HDF cells) were seeded on 96-well plates at a density of $10^4$ cells per well, and cultured in 100 microliters of Dulbecco's Modified Eagle Medium (DMEM) supplemented with 10% FBS, 5% penicillin-streptomycin, 2 mM L-glutamine, 4.5 g/L D-glucose and 110 mg/L sodium pyruvate, and incubated at 37° C., 5% $CO_2$ for 24 hours. Polymers were dissolved in the cell culture medium at various concentrations. The prepared solution (100 microliters) was then used to substitute the medium in each well. Each condition was tested in six replicates. The plates were then incubated at 37° C., 5% $CO_2$ for 6 hours. After 6 hours of treatment with the polymer, 100 microliters of fresh culture medium and 20 microliters of MTT solution (5 mg/mL) were added to replace the solution in each well. The plates were then maintained at 37° C., 5% $CO_2$ for 4 hours. After removing the medium, dimethyl sulfoxide (150 microliters) was added to each well to dissolve the internalized purple formazan crystals. The absorbance readings of formazan crystals were taken to be that at 550 nm subtracted by that at 690 nm (TECAN, Switzerland). Cell viability was expressed as a percentage of absorbance of the control cells without any treatment.

Figure 19:
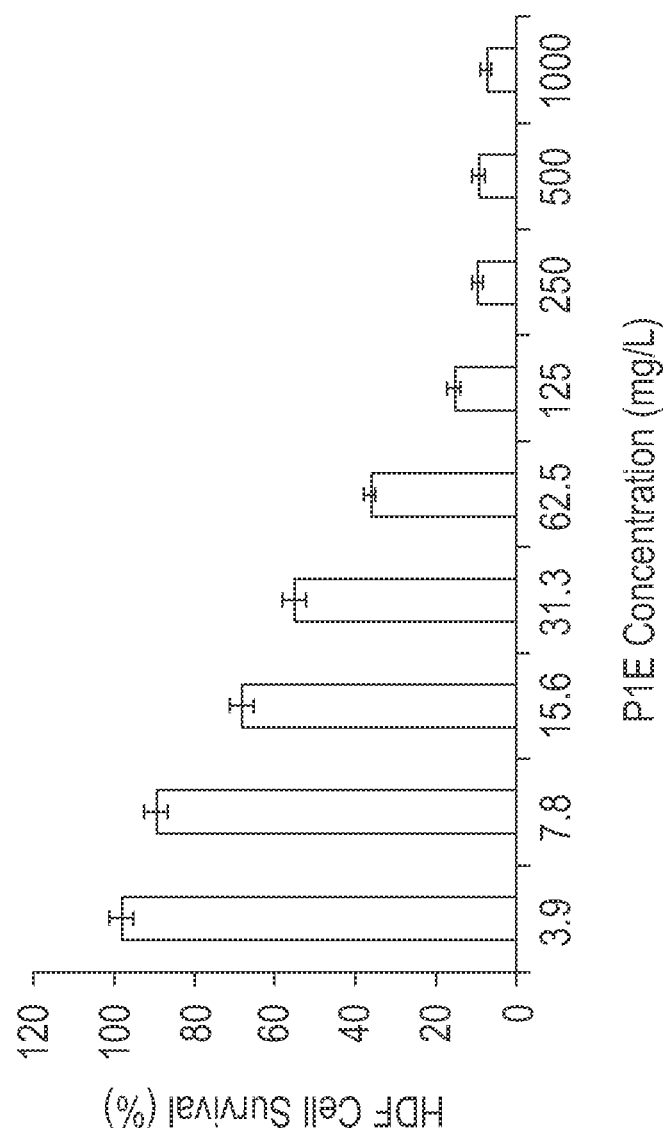
FIG. 19 is a bar graph showing the viability of human dermal fibroblast (HDF) cells after 6 hours of treatment with various concentrations of cationic polymer PIE.
Figure 20:
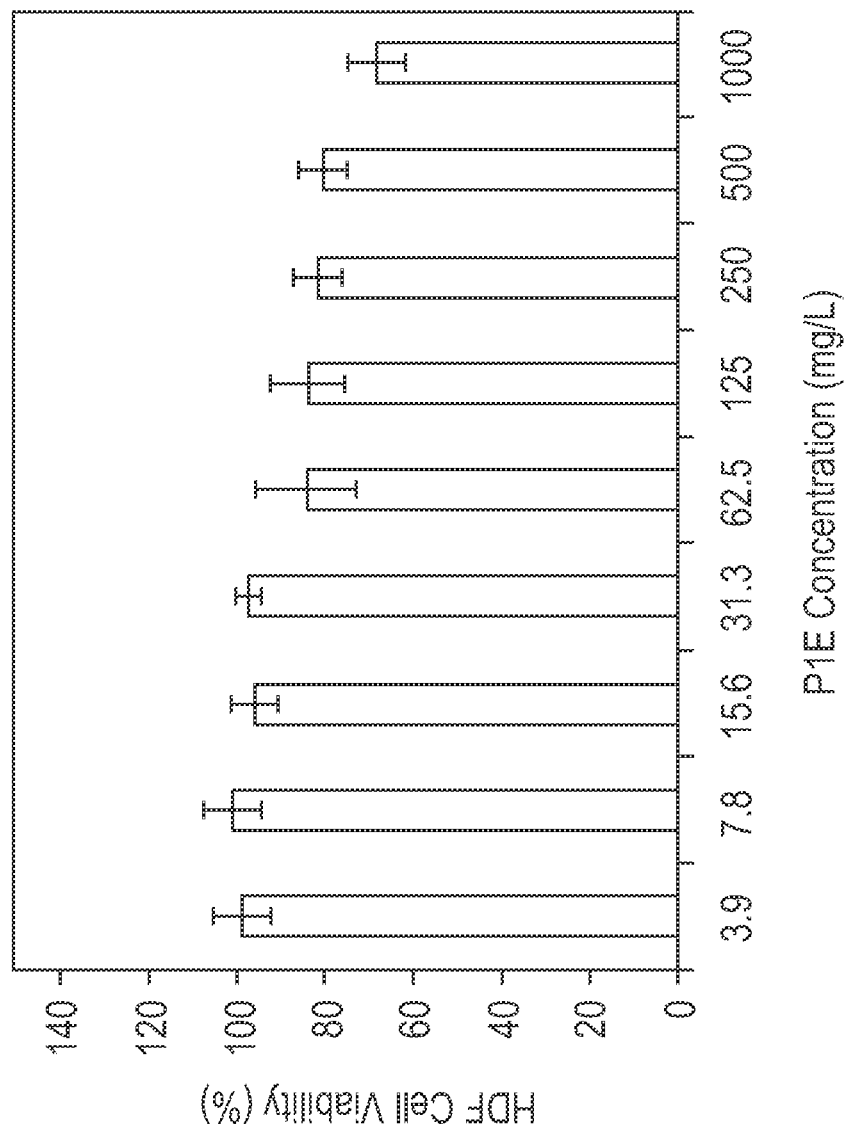
FIG. 20 is a bar graph showing the viability of human dermal fibroblast (HDF) cells after 2 minutes of treatment with various concentrations of cationic polymer PIE.

Viability of HDF cells was more than 60% after 6 hours of treatment with PIE at 15.6 mg/L (FIG. 19). Cell viability was about 80% even at 500 mg/L after 2 minutes of treatment (in the case of a hand wash) (FIG. 20). These data demonstrate that PIE has utility for use in laundry and as hand wash for surgeons.

CONCLUSION

Antimicrobial polymers were successfully synthesized via bulk addition polymerization reaction using commercially available inexpensive starting materials. Polymers P1E, P1EE, P2E8B, P2E6B, P2E4B, P2EE8BP, and P2EE6BP have broad-spectrum antimicrobial activity with fast killing kinetics. P1E, P1EE, P2E8B, P2EE8BP, and P2EE6BP do not induce significant hemolysis at concentrations of up to 1000 mg/L and are non-cytotoxic at their MIC concentrations. Therefore, the polymers are attractive materials for use in laundry, cosmetics and hand washes.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A cationic polymer comprising:
i) a cationic repeat unit of formula (C-1):

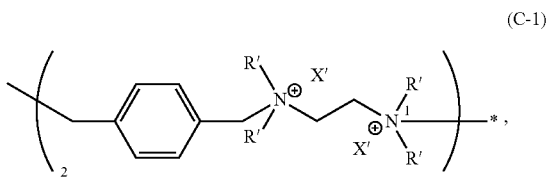

(C-1)

wherein
atomic centers nitrogen 1 and carbon 2 of formula (C-1) are labeled,
each X' is an independent negative-charged counterion, and
each R' is an independent monovalent radical selected from the group consisting of methyl, ethyl and propyl, and
ii) a second cationic repeat unit of formula (C-3):

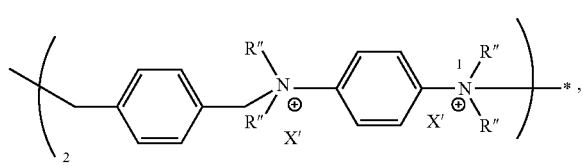

(C-3)

wherein
atomic centers nitrogen 1 and carbon 2 of formula (C-3) are labeled,
each X' is an independent negative-charged counterion, each R" is an independent monovalent radical selected from the group consisting of methyl, ethyl and propyl;
wherein the cationic repeat units of formula (C-1) and formula (C-3) are covalently linked.

2. The cationic polymer of claim 1, wherein each X' of formulas (C-1) and (C-3) is an independent anion selected from the group consisting of chloride, bromide, and iodide.

3. The cationic polymer of claim 1, wherein the cationic polymer is toxic to a microbe selected from the group consisting of Gram-positive microbes, Gram-negative microbes, fungi, and combinations thereof.

4. The cationic polymer of claim 1, wherein each R' is ethyl.

5. The cationic polymer of claim 1, wherein the cationic polymer has a number average molecular weight of about 1,000 to about 10,000.

6. The cationic polymer of claim 1, wherein each R' is methyl.

7. The cationic polymer of claim 1, wherein each X' of formulas (C-1) and (C-3) is a chloride ion.

8. The cationic polymer of claim 1, wherein each R' is propyl.

9. The cationic polymer of claim 1, wherein the cationic polymer is a random copolymer.

10. The cationic polymer of claim 1, wherein the cationic polymer comprises the cationic repeat units of formulas (C-1) and (C-3) in a (C-1):(C-3) molar ratio of 90:10 to 10:90.

11. The cationic polymer of claim 1, wherein each R" is methyl.

12. An antimicrobial composition, comprising the cationic polymer of claim 1 and a second component.

13. The antimicrobial composition of claim 12, wherein the composition is an aqueous mixture of the cationic polymer.

14. The antimicrobial composition of claim 12, wherein the antimicrobial composition is selected from the group consisting of laundry detergents, cosmetics, soaps, hand washes, lotions, and contact lens disinfectants.

15. The antimicrobial composition of claim 12, wherein the cationic polymer is a random copolymer of (C-1) and (C-3).

16. A method of killing a microbe, comprising contacting the microbe with the cationic polymer of claim 1.

17. The method claim 16, wherein the cationic polymer is a random copolymer of (C-1) and (C-3).

18. A method of forming the cationic polymer of claim 1, comprising:
forming a reaction mixture comprising i) a solvent, ii) an electrophilic agent of structure

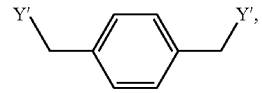

wherein each Y' is an independent leaving group selected from the group consisting of chloride, bromide, iodide, mesylate, and tosylate, and each Y' is capable of undergoing a nucleophilic substitution reaction with a tertiary amine to form a positive-charged quaternary amine, iii) a first nucleophilic agent comprising two nitrogens of two tertiary amine groups, wherein the two nitrogens of the first nucleophilic agent are linked by an ethane-1,2-diyl group (*—CH$_2$CH$_2$—*), and iv) a second nucleophilic agent comprising two nitrogens of two tertiary amine groups, wherein the two nitrogens of the second nucleophilic agent are linked by a benzene-1,4-diyl group:

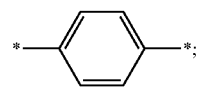

and
heating the reaction mixture at an elevated temperature with agitation, thereby forming the cationic polymer by addition polymerization of the electrophilic agent, the first nucleophilic agent, and the second nucleophilic agent, wherein the cationic polymer is not soluble in the solvent at the elevated temperature.

19. A cationic polymer, comprising a cationic repeat unit of formula (C-3):

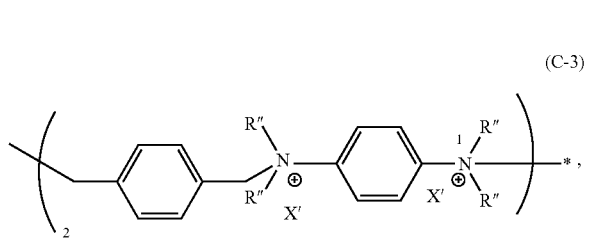

(C-3)

wherein
atomic centers nitrogen 1 and carbon 2 are labeled,
each X' is an independent negative-charged counterion,
each R" is an independent monovalent radical selected from the group consisting of methyl, ethyl and propyl.

20. The cationic polymer of claim 19, wherein the cationic polymer is a homopolymer.

21. The cationic polymer of claim 19, wherein the cationic polymer is a random copolymer comprising a second cationic repeat unit of formula (C-5):

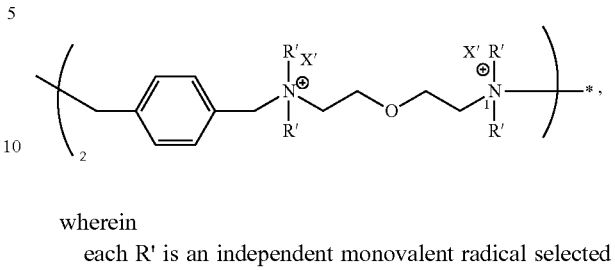

wherein
each R' is an independent monovalent radical selected from the group consisting of methyl, ethyl and propyl, and
each X' is an independent negative-charged counterion.

22. An antimicrobial composition, comprising the cationic polymer of claim 19 and a second component.

23. The antimicrobial composition of claim 22, wherein the cationic polymer is a homopolymer.

* * * * *